United States Patent
Zambounis et al.

[11] Patent Number: 5,830,267
[45] Date of Patent: Nov. 3, 1998

[54] COLORATION OF HIGH MOLECULAR WEIGHT ORGANIC MATERIALS IN THE MASS WITH SOLUBLE PHTHALOCYANINE PRECURSORS

[75] Inventors: John Zambounis, Basel; Heinz Wolleb, Marly, both of Switzerland

[73] Assignee: Ciba Specialty Chemicals Corporation, Tarrytown, N.Y.

[21] Appl. No.: 642,178

[22] Filed: May 6, 1996

[30]     Foreign Application Priority Data

May 12, 1995 [CH]  Switzerland ............................. 1394/95
Jul. 19, 1995 [EP]  European Pat. Off. ............. 95810472

[51] Int. Cl.$^6$ .................................................. C09C 67/50
[52] U.S. Cl. .................................. 106/413; 8/444; 8/661; 106/410; 106/411; 502/163; 524/88; 540/122
[58] Field of Search ..................... 8/661, 444; 502/163; 524/88; 540/122; 106/410, 411, 413

[56]                References Cited

U.S. PATENT DOCUMENTS

| | | | |
|---|---|---|---|
| 2,662,896 | 12/1953 | Pedersen | 8/661 |
| 2,662,897 | 12/1953 | Pedersen | 540/130 |
| 3,759,947 | 9/1973 | Pugin et al. | 540/128 |
| 5,718,998 | 2/1998 | Takahashi et al. | 430/76 |

FOREIGN PATENT DOCUMENTS

| | | |
|---|---|---|
| 0514093 | 11/1992 | European Pat. Off. . |
| 0648770 | 4/1995 | European Pat. Off. . |
| 0648817 | 4/1995 | European Pat. Off. . |
| 0654711 | 5/1995 | European Pat. Off. . |

*Primary Examiner*—Mark L. Bell
*Assistant Examiner*—Scott L. Hertzog
*Attorney, Agent, or Firm*—Kevin T. Mansfield

[57]                ABSTRACT

The invention relates to the coloration of high molecular weight organic materials in the mass with soluble phthalocyanine precursors of structure

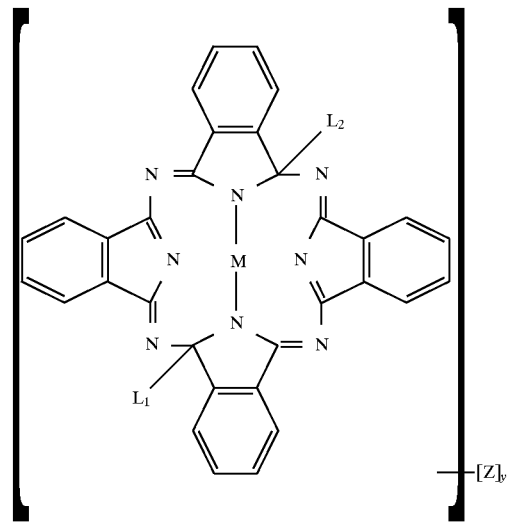

or isomers thereof, to the soluble phthalocyanine precursors as such wherein M is Zn, Ti or V or wherein $L_1$ is morpholino, pyrrolidino or with $C_1$–$C_{12}$alkyl substituted piperidino, to compositions containing high molecular weight organic materials and the above soluble phthalocyanine precursors, and to a process for making structured color images and applications thereof.

21 Claims, No Drawings

COLORATION OF HIGH MOLECULAR WEIGHT ORGANIC MATERIALS IN THE MASS WITH SOLUBLE PHTHALOCYANINE PRECURSORS

The present invention relates to the colouration of high molecular weight organic materials in the mass with soluble phthalocyanine precursors, to some soluble phthalocyanine precursors as such, to novel compositions containing high molecular weight organic materials and soluble phthalocyanine precursors, as well as to a process for making structured colour images and applications thereof.

Phthalocyanine pigments have been used for a long time as blue and green colourants. They give bright and deep hues having excellent characteristics, particularly high light stability. However, phthalocyanine pigments are still not satisfactory in some aspects, for instance it is difficult to incorporate homogeneously transparent phthalocyanine pigments of very fine particle size in polymeric materials at high concentrations due to rheology problems, or unwanted crystal growth or changes of the crystal modification may occur upon contact with organic solvents.

Phthalocyanine precursors (also sometimes called phthalocyanine-propigments or leucophthalocyanines) and their conversion to phthalocyanine colourants have been described by F. Baumann et al. [Angew. Chem. 68, 133–168 (1956) and U.S. Pat. No. 2,683,643] as well as by C. J. Pedersen [J. Org. Chem. 22, 127–132 (1957), U.S. Pat. No. 2,662,895, U.S. Pat. No. 2,662,896 and U.S. Pat. No. 2,662,897]. However, the processes described by these authors do not provide the means to colour high molecular weight organic materials in the mass, since the pigment is formed in aqueous or alcoholic solution at the surface of the materials to be coloured.

The colouration of high molecular weight organic materials in the mass with substituted pigment precursors containing carbamate groups is described in EP 648 770, EP 648 817 and EP 654 711. However, this method can only be applied to pigments containing reactive —NH— or —NH$_2$ groups, which is not the case of usual industrial phthalocyanine pigments.

Alternatively to insoluble phthalocyanine pigments, it is also possible to use soluble dye derivatives thereof, such as the above-mentioned carbamates, but the colourations obtained with these soluble phthalocyanine dye derivatives are not satisfactory as for the poorer migration resistance and, particularly, the poorer light and heat stability.

Highly surprisingly, it has now been found that some particular soluble phthalocyanine precursors are especially useful to colour high molecular weight organic materials in the mass, with excellent results in terms of migration, light and heat stability as well as homogenity, even at high concentrations and with pigments of small particle size.

The present invention relates therefore to a process for the colouration of high molecular weight organic materials in the mass, wherein a soluble phthalocyanine precursor, selected from the group consisting of compounds of formulae (I) to (VII),

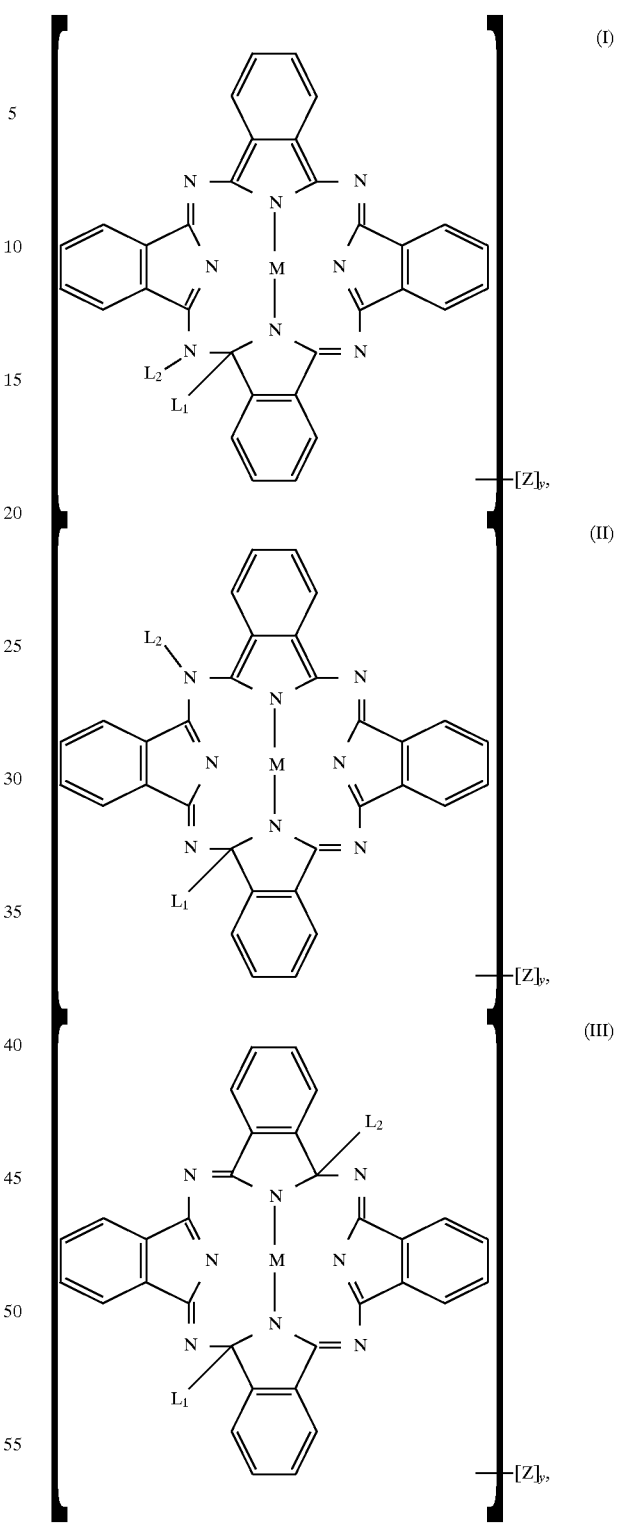

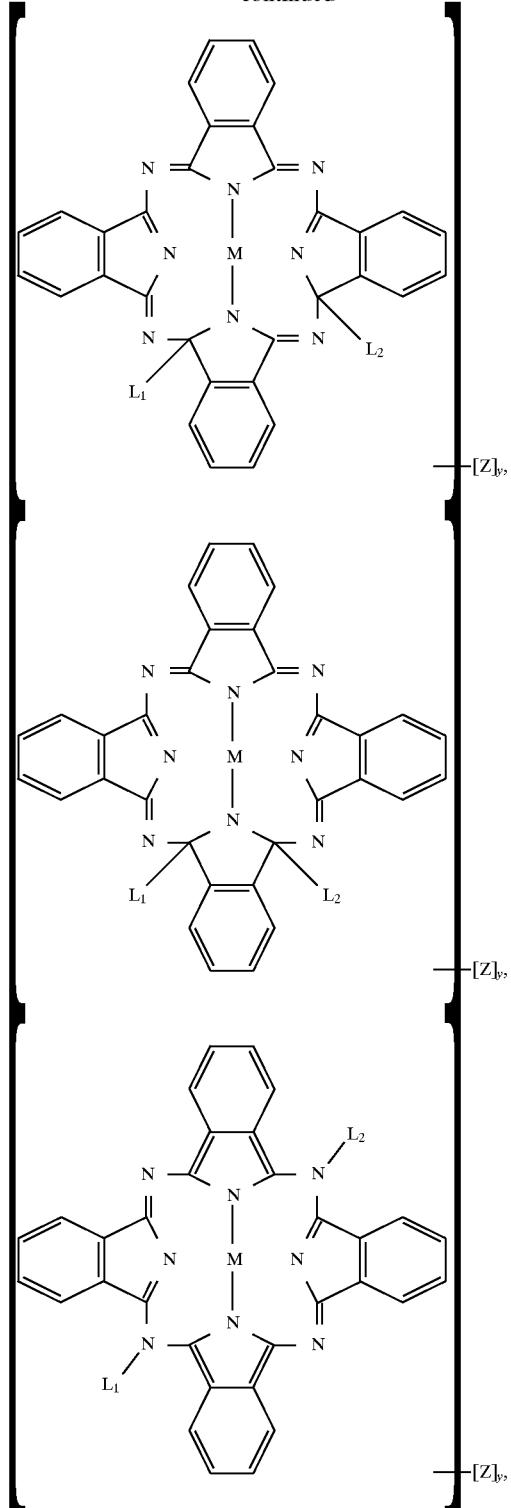

(IV)

(V)

(VI)

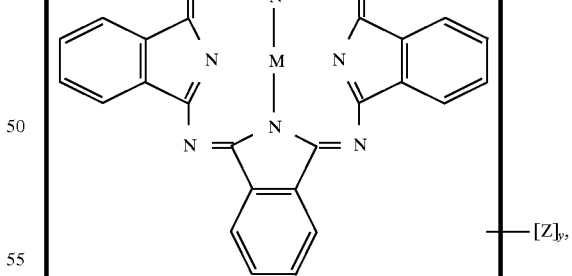

(VII)

wherein $L_1$ and $L_2$ are independently from each other halogen, $C_1$–$C_{18}$alkoxy, $C_1$–$C_{18}$alkylthio, $C_1$–$C_{18}$alkylamino, $C_2$–$C_{18}$ dialkylamino, or an unsubstituted or with 1 or 2 $C_1$–$C_{12}$alkyl groups substituted 5- or 6-membered imino ring which contains zero or one additional nitrogen or oxygen atom, M is two hydrogens, two metals with one valence or a metal with two or more valences, y is a number from 0 to 16, and each Z is independently of the other halogen, $C_1$–$C_{18}$alkyl, $C_1$–$C_{18}$alkoxy, $C_1$–$C_{18}$alkylthio or $C_2$–$C_{18}$dialkylamino, is added to the high molecular weight material, and wherein said high weight organic material containing a compound of formula (I) to (VII) in the mass is heated to at least 130° C., or is exposed to a radiation of wavelength 250–500 nm, whereby said compound of formula (I) to (VII) is converted, essentially in the absence of water, into a compound of formula (VIII)

(VIII)

wherein M, y and Z have the same meaning as above.

The 5- or 6-membered imino rings which may contain one additional nitrogen or oxygen atom are N-bound heterocycles which are preferably saturated, such as for example morpholino, 2,6-dimethyl-morpholino, piperidino, pyrrolidino, imidazolidino, N-methyl-imidazolidino, piperazino or N-methyl-piperazino. If the 5- or 6-membered ring imino residue is substituted with $C_1$–$C_{12}$alkyl, then preferably with linear $C_1$–$C_6$alkyl, most preferably with n-propyl. If the 5- or 6-membered ring residue contains one additional nitrogen atom, then this additional nitrogen atom is preferably substituted with linear $C_1$–$C_6$alkyl.

$L_1$ and $L_2$ are preferably $C_2$–$C_{18}$dialkylamino, morpholino, pyrrolidino or unsubstituted or with $C_1$–$C_{12}$alkyl substituted piperidino, most preferably with $C_1$–$C_{12}$alkyl substituted piperidino, particularly 4-n-propyl-piperidino.

M is for example $H_2$, $Li_2$, $K_2$, $Na_2$, Mg, Ca, Ti, V, Mn, Cr, Fe, Co, Ni, Cu, Zn, Zr, Pd, Cd, Sn, Ce, Hg, Pb or Bi, preferably $H_2$, Zn, Cu, Ni, Fe, Ti or V, most preferably $H_2$, Zn or Cu.

y is preferably a number 0, 4 or 8, most preferably 0.

Z is preferably halogen, $C_1$–$C_{18}$alkyl or $C_1$–$C_{18}$alkoxy, most preferably halogen.

Halogen is bromo, chloro, fluoro or iodo, preferably bromo or chloro, most preferably chloro.

$C_1$–$C_{18}$alkyl is for example methyl, ethyl, n-propyl, isopropyl, n-butyl, sec-butyl, tert-butyl, n-amyl, tert-amyl, hexyl, heptyl, octyl, 2-ethylhexyl, nonyl, decyl, dodecyl, tetradecyl, hexadecyl or octadecyl, preferably linear $C_1$–$C_6$alkyl such as methyl, ethyl, n-propyl, n-butyl, n-amyl or hexyl, most preferably methyl.

$C_1$–$C_{18}$alkoxy stands for —O—$C_1$–$C_{18}$alkyl, $C_1$–$C_8$alkylmercapto for —S—$C_1$–$C_8$alkyl, and $C_1$–$C_8$alkylamino for —NH—$C_1$–$C_{18}$alkyl; $C_2$–$C_{18}$dialkylamino stands for a tertiary amino group, wherein the number of carbon atoms of both alkyl substituents is added. In those cases, the same alkyl groups are preferred as above.

Illustrative examples of high molecular weight organic materials which can be coloured with the compounds of formulae (I) to (VII) are:

polymers based on vinyl compounds, such as polystyrene, poly-α-methylstyrene, poly-p-methylstyrene, poly-p-hydroxystyrene, poly-p-hydroxyphenylstyrene, polyacrylates such as poly(methylacrylate) and poly(acrylamide), polymethacrylates such as poly(methylmethacrylate), poly(methylmaleate), poly(acrylonitrile), poly(methacrylonitrile), poly(vinylchloride), poly(vinylfluoride), poly(vinylidenechloride), poly(vinylidenefluoride), poly(vinylacetate), poly(vinylalcohol), poly(methylvinylether) and poly(butylvinylether), polyolefins such as polyethylene and polypropylene, and polyalkadienes such as polybutadiene, polymers formed from maleimides and/or maleic anhydrides such as copolymers from maleic anhydride and styrene, poly(vinyl pyrrolidon), as well as copolymers of two or more of these compounds such as ABS or poly(vinylchloride/vinylacetate/vinylalcohol);

polyesters such as particularly polyethylene terephthalate, polycarbonates;

novolacs derived from a $C_1$–$C_6$-aldehyde, e.g., formaldehyde or acetaldehyde, and a mononuclear or dinuclear, preferably mononuclear, phenol which may optionally be substituted by one or two $C_1$–$C_9$alkyl groups, by one or two halogen atoms or by one phenyl nucleus, such as o-, m- or p-cresol, xylenol, p-tert.-butylphenol, o-, m- or p-nonylphenol, p-chlorophenol or p-phenylphenol, or those with more than one phenolic group, such as resorcin, bis-(4-hydroxyphenyl)methane or 2,2-bis-(4-hydroxyphenyl)propane;

biopolymers and their derivatives, such as cellulose, starch, chitin, chitosan, gelatine, zein, cellulose derivatives, for example ethylcellulose, nitrocellulose, celluloseacetate and cellulosebutylate; and natural and synthetic resins, such as rubber, waxes, casein, silicon, silicone resins, urea-formaldehyde and melamine-formaldehyde resins, alkyd resins, phenolic resins, polyamides, polyaramides, polyimides, polyamide/imides, polysulfones, polyethers such as polyphenylene oxides, polybutyral, polyethersulfones, polyurethanes, polyureas, polyarylenes, polyarylenesulfides, epoxy resins such as polyepoxides.

The above high molecular weight organic compounds may be used singly or as mixtures in the form of rigid or plastic materials, melts or spinning solutions, paint systems, coating materials or printing inks.

Of very great importance is the unexpected easy conversion of the soluble phthalocyanine precursors of formula (I) to (VII) to the corresponding insoluble phthalocyanine pigments of formula (VIII), within the polymeric substrate in which they are incorporated.

This can be done either by thermal treatment (heating to the temperature range from 130°–400° C., preferably to 160°–250° C., for example through exposure to hot gases or to infrared radiation), or by photolytic treatment (exposure to light) at wavelength 250–500 nm, preferably around 300 nm or 450 nm, most preferably around 300 nm (the phthalocyanine precursor's main absorption band), of the solid or plastic materials, melts, solutions or dispersions containing the soluble phthalocyanine precursors. Infrared (IR) radiation as a source of heat has a wavelength of 800–10600 nm and comes preferably from a laser. The thermal and photolytic treatments can also be simultaneously or sequentially combined.

Additional water-carried inorganic chemicals, such as reducing agents like sodium hydrosulfite and acids or bases like hydrochloric acid or sodium hydroxide, are surprisingly not required in order the instant process to work satisfactory. Additional light-sensitive compounds such as diazonium salts are not required either. Such not requisited reactive or caustic compounds generally prejudice the pigment's and/or polymer's durability. The instant process is therefore run essentially in the absence of water. Preferably, it is run essentially in the absence of any compound which is caustic or reactive with the precursor of formula (I) to (VII), with the pigment of formula (VIII) or with the high molecular weight organic material upon heating to 130°–400° C. or upon exposure to light of wavelength 250–500 nm. Most preferably, heating is achieved through IR radiation from a laser.

The ease with which the soluble phthalocyanine precursors of formulae (I) to (VII) can be converted into the corresponding phthalocyanine pigments of formula (VIII) after their incorporation into the substrate also renders a separate conversion step superfluous when the high molecular weight organic material is processed at temperatures above 130° C., preferably above 200° C. or, most preferably, 200°–220° C. In this case, the precursor is converted into the pigment at the time of processing, avoiding any changes having to be done in the manufacturing process. This may happen for instance during the extrusion of high density polyethylene granulates, while casting a polycarbonate object through injection molding, upon melt spinning polypropylene fibers or upon curing a paint, coil coating or powder coating composition, as well as in many other high temperature applications well-known in the art.

The instant process is particularly suitable for the mass colouration of high molecular weight organic materials which are essentially impermeable to water and aqueous solvents, such as polyesters, polyvinyl chloride, ABS and, preferably, polyolefins such as polyethylene and polypropylene, as well as coating materials, including paint systems and powder coating compositions. In particular, it gives excellent results in applications wherein homogeneous colourations are desirable and wherein aggregates are unacceptable, such as in fibres, inkjet or colour filters for liquid crystal displays. Owing to the benefits of the precursor's dry conversion to pigments within the binder after the printing operation, it can also be used advantageously for printing inks.

The present invention relates therefore also to a composition comprising (a) a soluble phthalocyanine precursor, selected from the group consisting of compounds of formulae (I) to (VII), and (b) a high molecular weight organic material which is essentially impermeable to water and aqueous solvents, wherein said soluble phthalocyanine precursor (a) is embedded in the mass of said high molecular weight organic material (b).

The soluble phthalocyanine precursors (a) are known and can be made as described by F. Baumann et al. [Angew. Chem. 68, 133–168 (1956) and U.S. Pat. No. 2,683,643] or by C. J. Pedersen [J. Org. Chem. 22, 127–132 (1957), U.S. Pat. No. 2,662,895, U.S. Pat. No 2,662,896 and U.S. Pat. No. 2,662,897]; new precursors can also be made from known compounds analogically by the same methods. The disubstituted dihydro phthalocyanines so obtained are for example of formula (III), as the compound (IIIA) of example 8 below. However, in most cases the disubstituted dihydro phthalocyanines are not of exactly known structure and could be any single compound of formulae (I) to (VII), as well as a mixture of two or more compounds of said formulae.

Moreover, each formula (I) to (VII) represents only one possible tautomeric form and takes no account of the distortion engendered by the introduction of the groups $L_1$ and $L_2$ and the decrease in electronic delocalization, which affect the planarity of the molecule and the bond lengths between the central metal atom and its four nitrogen neighbors [see also R. P. Linstead et al., J. Chem. Soc. 1934, 1033–9 (1934)]. Hence, formulae (I) to (VII) are to be considered as equivalent to similar formulae expressing only minor differences in geometry or electron distribution, such as for example the tautomeric formulae (IXa) and (IXb):

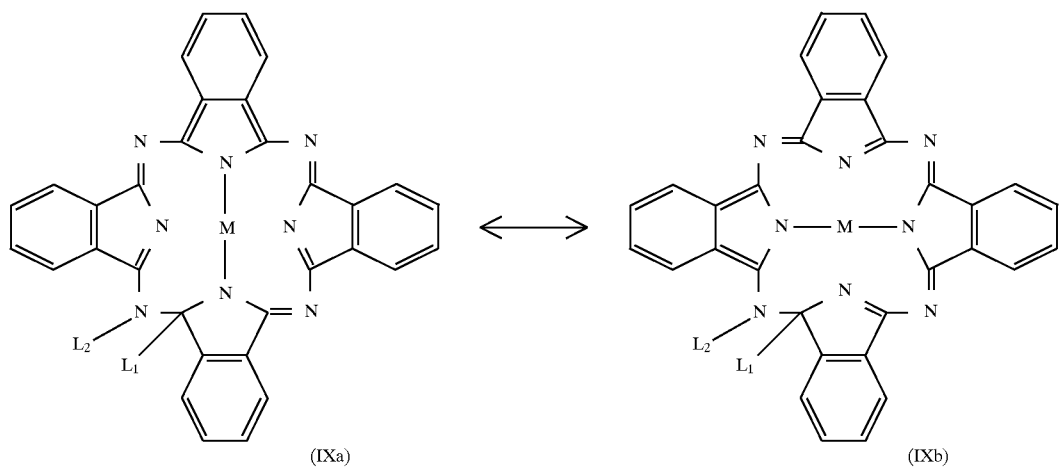

(IXa)                                            (IXb)

We believe that, depending on the nature of the substituents $L_1$, $L_2$ and Z and on the reaction conditions, some or others compounds of formulae (I) to (VII) are formed to variable extent. Said compounds may perhaps also be converted into each other through isomerisation, for example upon dissolution in a protic solvent in presence of an acid or basic catalyst, or upon heating at an elevated temperature such as between 50° C. and the decomposition point. This does however not affect their use in the present invention.

The soluble phthalocyanine precursor (a) can be used in amounts of 0.01 to 70% by weight, based on the high molecular weight organic material (b) to be pigmented. If the pigmented material is intended for end use, such as a granulate for use in injection moulding for the manufacture of objects, preferably the soluble phthalocyanine precursor is used as a toner in amounts of 0.1 to 10% by weight.

Depending on the end use requirements, it may however be particularly convenient to use the soluble phthalocyanine precursor (a) in the form of preparations such as masterbatches, which can themselves be added to colourless high molecular weight organic material as colourants. In this case, the soluble phthalocyanine precursor is preferably used in amounts of 5 to 70% by weight, most preferably 20 to 4.0% by weight, based on the high molecular weight organic material of the preparation or masterbatch.

High molecular weight organic materials essentially impermeable to water and aqueous solvents are such which do not absorb significant quantities of water and aqueous solvents (e.g. ≦3% by weight) and do not swell in water (e.g. ≦3% volume increase). This intrinsic characteristic of the material should not be confused with the permeability of objects made out of it, as of a microporous membrane made of in fact water-impermeable polyethylene.

Amongst the above mentioned high molecular weight organic materials, some examples of such which are essentially impermeable to water and aqueous solvents are polystyrenes, poly(vinylchloride), polyethylene, polypropylene, polybutadiene, ABS, polyesters such as polyethylene terephthalate, polycarbonates, melamine-formaldehyde resins, alkyd resins, novolacs, polyamides, polyaramides, polyimides, polysulfones, polyethers such as poly-phenylene oxides, polyethersulfones, polyarylenes, polyarylenesulfides and epoxy resins.

The colouration of bulk high molecular weight organic materials in the mass with phthalocyanine precursors (a) is suitably effected by incorporating the soluble phthalocyanine precursor in the masterbatch or end use substrate using roll mills, mixing or milling apparatus. The coloured material is then brought into the desired final form by methods which are known per se, conveniently by calendering, moulding, extruding, coating, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. The plasticisers may be incorporated before or after blending the soluble phthalocyanine precursors into the polymers. To obtain different shades it is also possible to add to the high molecular weight organic materials, in addition to the soluble phthalocyanine precursor, any amount of fillers or other components, such as white, coloured, black, or colourless or coloured metallic or flop effect pigments.

For pigmenting paint systems, coating materials and printing inks, the high molecular weight organic material and the soluble phthalocyanine precursor are dissolved or finely dispersed in a common organic solvent or mixture of solvents, optionally together with additives such as fillers, other pigments, siccatives, plasticisers or stabilizers. The procedure may be such that the individual components by themselves, or also several components together, are dissolved or dispersed in the solvent before mixing with the other components.

Examples of solvents wherein the high molecular weight organic material and the soluble phthalocyanine precursor can be dissolved or finely dispersed are ethers, such as tetrahydrofuran and dioxane; glycolethers, such as ethyleneglycol-methylether, ethyleneglycol-ethylether, diethyleneglycol-monomethylether and diethyleneglycol-monoethylether; aprotic solvents, such as acetonitrile, benzonitrile, N,N-dimethylformamide, N,N-dimethylacetoamide, nitrobenzene, N-methylpyrrolidone, halogenated aliphatic or aromatic hydrocarbons, such as trichloromethane, benzene unsubstituted or substituted with alkyl, alkoxy or halogen, such as toluene, xylene, anisole and chlorobenzene, and aromatic N-heterocycles, such as pyridine, picoline and quinoline; alcohols, such as methanol, ethanol and diacetone alcohol; carboxylates and lactones, such as propylene carbonate, ethyl acetate, methyl propionate, ethyl benzoate, γ-butyrolactone and γ-valerolactone; sulfoxides, such as dimethyl sulfoxide; sulfones, such as dimethyl sulfone and diethyl sulfone; and ketones, such as dimethyl ketone, methyl ethyl ketone and cyclohexanone and others; water may be used for water-soluble components such as poly(vinyl alcohol).

Water and alcohols cannot be used as main solvents for water-impermeable high molecular weight organic materials. Water may however be tolerated in traces (e.g. $\leq 2\%$ by weight) and alcohols may be used as minor cosolvents (e.g. $\leq 10\%$ by weight) for some polymers, such as for example vinyl polymers.

The high molecular weight organic materials coloured by the instant method show excellent, unexpectedly enhanced coloristic properties such as brilliant hues, high colour strength, high transparency, and good fastness to migration, light and weathering. The single phthalocyanine pigment particles are small, preferably $\leq 1$ μm, most preferably $\leq 0.1$ μm, essentially not aggregated, and excellently dispersed in the polymer even at high concentrations, notably also at concentrations $\leq 5\%$ by weight, based on the weight of the high molecular weight organic material. In a preferred embodiment, the number of aggregates, defined as particles the length of which is treble the average length of a single pigment particle or more, does not exceed 3% of the total number of phthalocyanine pigment particles.

The soluble phthalocyanine precursors of formulae (I) to (VII), wherein $L_1$ stands for or an unsubstituted or with 1 or 2 $C_1$–$C_{12}$alkyl groups substituted 5- or 6-membered imino ring which contains zero or one additional nitrogen or oxygen atom, with the proviso that $L_1$ is not unsubstituted piperidino, or wherein M stands for Zn, Ti or V, are new. Thus, the invention comprises also a soluble phthalocyanine precursor, selected from the group consisting of compounds of formulae (I) to (VII), wherein LI is an unsubstituted or with 1 or 2 $C_1$–$C_{12}$alkyl groups substituted 5- or 6-membered imino ring which contains zero or one additional nitrogen or oxygen atom, with the proviso that $L_1$ is not unsubstituted piperidino, or wherein M is Zn, Ti or V.

The invention relates further to novel compositions for making structured colour images. As methods for forming polymer pattern or image layers, there are known various techniques like photolithography, impact printing, such as screen printing, gravure printing, flexo printing and offset printing, non-impact printing, such as ink-jet printing, thermal dye diffusion transfer, laser marking, electrodeposition, etc.

In all these known imaging and recording methods, the actual colouring material comprises pigments and dyestuffs combined with appropriate resins, binders, polymers and additives.

Such colours are thus applied, for example, as recording elements of optical memories as disclosed in JP Kokai 05050757 A, as recording elements of thermal recording memories as disclosed in EP 535 788, or as colouring materials for colour filters of LCDs (liquid crystal displays) as described by H. Aruga, J. Photopolym. Sci. Technol. 3(1),9–16 (1990), EP 380 223, K. Mizuno et al., Jpn. J. Appl. Phys. 30/Part 1, 3313–17 (1991) and K. Kobayashi, Solid State Technology 11, 15–18 (1992). Polymeric pattern layers may also be coloured after crosslinking, for example through thermal dye diffusion transfer with well-known dyes as mentioned in EP 008 828.

According to the above literature, pigments and dyestuffs are used in the form of compositions containing pigments or dyestuffs, polymers or prepolymers and optionally other additives, which are subject to image formation in order to achieve recording or to form coloured patterns. The process usually comprises the polymerization of a prepolymer or the depolymerization of a structurable polymer by applying heat or electromagnetic radiation or the combination thereof, and the subsequent development using appropriate developers; alternatively, pigments or dyestuffs may be applied directly in a selective pattern, for example through non-impact printing.

While dyes in general are deficient in terms of light, heat, solvent and chemical resistance, pigments in such applications show problems related to dispersion and dispersion stability, transparency, profile sharpness of absorption or transmission spectra and/or lack of solubility or diffusibility. Many properties desirable for the dye's or pigment's neat incorporation into critical systems such as colour LCD's are contradictory with such required for high quality applications. Unsatisfactory compromises have thus to be complied with, like in JP Kokai 60/180889 where stability is obtained at the cost of low optical reflection density and poor colour gamut, and many pigments cannot be used at all.

Recent development in imaging and recording technology requires, however, compositions for producing patterns or images with higher transparency (i.e. high light transmittance), especially for colour filter of LCDs, higher contrast ratio, higher colour purity and strength, higher pattern resolution and precision of image, no (dye) colour mixing, no clogging of sieves during purification of colour/polymer mixtures, smoothness of image surface, pinhole free and noncontaminated image layer, higher registration accuracy, higher sharpness of image edges, higher thermal, chemical and light stability, and ultra thin film characteristics.

The compositions described in EP 654 711, containing pigment derivatives which are substituted at —NH— or —NH$_2$ groups, resolve the above problems in part. However, usual industrial phthalocyanine pigments contain nitrogen only as =N— groups and do not react to urethanes with dicarbonates, trihaloacetic acid esters and similar reagents. Hence, one cannot obtain structured colour images containing phthalocyanines which hold nitrogen only as =N— groups with the EP 654 711 disclosure. It has now been found that soluble pigment precursors of formulae (I) to (VII) can be surprisingly easily transformed by thermal or photolytical means into insoluble nano-sized pigment particles of formula (VIII), and that the compositions containing said pigment precursors satisfy the aforementioned requirements for structured colour images much better than those of the prior art.

Furthermore, the present compositions containing phthalocyanines precursors of formulae (I) to (VII) have surprisingly superior properties, notably generating under mild conditions structured colour images of even higher colour light and heat stability, as compared with the compositions of EP 654 711 containing substituted phthalocyanines.

The invention therefore comprises also a composition for making structured colour images comprising (a') a soluble phthalocyanine precursor, selected from the group consisting of compounds of formulae (I) to (VII), and (b') a positive or negative resist-type resin, polymer or prepolymer which can be structured by crosslinking, polymerisation or depolymerization by applying heat or by irradiation.

As component (a') of the instant composition a single compound or a combination of two or more compounds of formulae (I) to (VII) may be used in the practice of the instant invention.

Component (b') of the instant compositions, the positive or negative resist-type resin, polymer or prepolymer eligible for use in the present invention are, for example, those which are described in EP 654 71 1, such as b'1) positive resists, such as diazoquinone resists based on phenolic resins such as novolac and diazonaphthoquinones;

b'2) negative resists, such as dichromated polymers such as dichromated gelatine, -starch, -poly(vinyl alcohol), -poly(vinylpyrrolidone), -poly(vinyl butyral) and -poly (amide acid) (PAA); polymers having crosslinking groups in side chains, such as poly(vinyl cinnamate), poly(vinyl cinnamylidene acetate), poly(vinyl alcohol) to which chalcone or phenylene diacrylate are attached, polyesters of p-phenylenediacrylic acid (PPDA) with glycols and polyesters based on styrylpyridine;

water processable resists, such as styrene-maleic anhydride copolymer, phenolic quaternary pyridinium salts; polymeric styrylquinolinium salts;

acrylic copolymers having dimethylmaleimide as a side chain; substituted poly(vinyl alcohol) containing diphenylcyclopropane as a side chain; poly(vinyl alcohol) and poly(vinylpyridine) to which a bifunctional acylsilane is added; azide resists based on poly(vinyl phenol) and mono-azides;

bis-azide resists based on poly(cis-isoprene) and bis-azides, such as 2,6-bis(4-azidobenzal)-4-methylcyclohexanone (ABC), 4,4'-diazidostilbene, 4,4'-diazidobenzophenone or 4,4'-diazidobenzalacetone;

water processable azido resists based on poly (acrylamide) or poly(vinylpyrrolidone) and water soluble bis-azides; polymers having azido groups;

photocrosslinking copolymers of vinyl benzophenone and 4-dimethylaminostyrene; photoreactive polyimides and diazoresins;

b'3) photopolymers containing monomers, such as acrylates, methacrylates, acrylamide and styrene; crosslinkers, such as 1,6-hexanediol diacrylate, triethyleneglycol diacrylate, N,N'-methylenebis(acrylamide), trimethylolpropanetriacrylate, pentaerythritol triacrylate and pentaerythritol tetraacrylate;

binders, such as polymers of the monomer used, polyesters, polyurethanes, nylons, polycarbonates and cellulose derivatives;

fillers, such as organophilic silicas and clays;

initiators, such as benzoin derivatives, anthraquinones plus hydrogen donors, and benzophenones and amines;

and stabilizers, such as p-methoxyphenol, hydroquinones and naphthols; especially those containing reactive binders, such as unsaturated polymers obtained by the condensation of maleic and fumaric acid with glycols, poly-functional acrylates based on bisphenol A and other polyfunctional prepolymers;

b'4) positive deep-UV (ultraviolet) resists, such as modified diazoquinone resist based on novolac and diazopyrazolidine dione, diazotetramic acid, diazopiperidine dione and diazo-Meldrum's acid; resists based on o-nitrobenzyl esters; m-poly(nitroanilide); poly(p-acetoxystyrene); o-nitrobenzyl-substituted polyethers; poly(methyl methacrylate) (PMMA) derivatives, such as 3-oximino-2-butanone methacrylate (OMMA)-MMA copolymer, OMMA-methacrylonitrile-MMA terpolymer, MMA-indenone copolymer; poly(methyl isopropyl ketone) (PMIPK); polymers containing triphenylcarbonium ions in their backbone; polycarbonates; poly(tert-butoxycarbonyloxystyrene), preferably with an onium salt acid generator; novolac with carbonates and onium salts or with naphthalene-2-carboxylic acid-tert-butyl ester; and copolymers of phthalaldehyde with o-nitrobenzaldehyde;

b'5) negative deep-UV resists, such as bis-azide-cyclized rubber composition containing 4,4'-diazidodiphenyl sulfide, bis-azide-poly(vinyl phenol) composition containing 3,3'-diazidodiphenyl sulfone and bis-azido-poly (methyl methacrylate) composition containing 3,3'-diazidodiphenyl sulfone, epoxides with onium salts or with n-hexyloxydiazonium hexaflurophosphate;

b'6) positive electron resists, such as PMMA derivatives, such as poly(perfluorobutylmethacrylate), poly(hexafluoro methacrylate), and especially poly(2,2,2-trifluoro-ethyl-α-chloroacrylate); poly(ortho-substituted 2-phenylethyl methacrylates); copolymers of MMA with methacrylic acid, acrylonitrile or methacrylic anhydride; terpolymers of MMA, methacrylic acid and methacrylic anhydride; poly(olefin sulfones), such as poly(butene sulfone); novolacs with poly(olefin sulfone), such as poly(2-methylpentene-1-sulfone) (PMPS); poly(p-tert-butoxycarbonyl oxystyrene); and polystyrene-tetrathiofulvalene;

b'7) negative electron resists, such as epoxydized polybutadiene, poly(glycidyl methacrylate) (PGMA), copolymers of glycidyl methacrylate with ethylacrylate (COP); copolymers of allyl methacrylate with hydroxyethyl methacrylate; copolymers of propargyl methacrylate with hydroxyethyl methacrylate; polystyrene based resists, such as iodinated polystyrene and poly(chloromethylstyrene); poly(chloromethylstyrene-co-2-vinyl naphthalene); poly(vinyl naphthalenes); poly(vinyl pyridine) quaternized with methyl iodine; diazoquinone-novolac photoresists; and Langmuir-Blodgett films of to-tricosenoic acid, (ω-tricocynoic acid and o-octadecyl acrylic acid;

b'8) positive X-ray resists, such as resist ®HPR-204 (Olin-Hunt);

b'9) negative X-ray resists, such as poly(2,3-dichloro-1-propyl acrylate) (DCPA), poly(chloro-methylstyrene) (PCMS), chlorinated poly(methylstyrene) (CPMS), copolymers of allyl methacrylate with 2-hydroxyethylmethacrylate or glycidylmethacrylate;

b'10) chemically or thermally effectable polymers, such as poly-p-hydroxystyrene or novolac with melamine crosslinker, which system undergoes crosslinking by applying heat in the presence of acid catalysts;
copolymers of p-hydroxystyrene and esterified p-hydroxymethylstyrene, which crosslink under the presence of acid;
COP resins which crosslink under the presence of amines;
latent polyamines which undergo crosslinking upon irradiation with light under the presence of bis-epoxide;
epoxy resins, such as glycidylated cresol novolac, bisphenol A diglycidyl ether, hydantoin-N,N'-bisglycide, propylene-1,3-bishydantoin-2-hydroxytriglycide, p-aminophenoltriglycide, diaminodiphenylmethanetetraglycide, vinylcyclohexene dioxide, 3,4-epoxycyclohexylmethyl-3,4-epoxycyclohexanecarboxylate and mixtures thereof, which crosslink in the presence of appropriate curing agents, such as polyamines, novolacs, polyaminoamides and polycarboxylic anhydrides; esters of poly(vinyl benzoic acid), which transform to poly(vinyl benzoic acid) by heating in the presence of catalytic amount of acid;
blocked poly-p-hydroxystyrenes, which transform to poly-p-hydroxystyrene by heating in the presence of catalytic amount of acid;
esters of polyacrylates and polymethacrylates, which transform to polyacrylic- or polymethacrylic acid by heating in the presence of catalytic amount of acid;
polycarbonates, which depolymerize under heating; and
mixtures of methacrylic acid-methyl methacrylate copolymer and methacryloyl chloride-methyl methacrylate copolymer, which crosslink by heating;

b'11) positive ion beam resists, such as poly(methyl methacrylate), poly(methylvinyl ketone), poly(tert-butyl methacrylate) and poly(butene sulfone);

b'12) negative ion beam resists, such as poly(vinyl acetate), poly(vinyl cinnamate), poly(methyl siloxane), poly(glycidyl methacrylate-co-ethyl acrylate), polystyrene, poly(4-chlorostyrene), poly(4-bromostyrene) and novolac;

b'13) silicon containing positive resists, such as poly(dimethylsiloxane), poly(phenylmethylsiloxane), and siloxane substituted propyl methacrylates; and b'14) silicon containing negative resists, such as copolymers of trimethylsilylmethyl styrene with chlorostyrene, chloromethylated poly(diphenyl siloxane), brominated poly(1-trimethylsilyl propylene), poly(triallyl phenylsilane) together with 2,6-bis(4'-azidobenzal)-methylcyclohexanone, and poly(trimethylsilylmethyl styrene) in combination with 1,2,4-trichlorobenzene and 3,3'-diazidodiphenyl sulfone.

Preferred components (b') of the instant compositions are positive resists of b'1), negative resists of b'2), photopolymers of b'3), positive deep-UV resists of b'4), negative deep-UV resists of b'5), and chemically and thermally effectable polymers of b'10).

Especially preferred are:

diazoquinone resists; dichromated polymers, such as dichromated gelatine, -starch, -poly(vinyl alcohol), -poly(vinylpyrrolidone), -poly(vinyl butyral) and -poly(amideacid);

polymers having crosslinking groups in side chains, such as poly(vinyl cinnamate), poly(vinyl cinnamylidene acetate), poly(vinyl alcohol) to which chalcone or phenylene diacrylate are attached, and polyesters of p-phenylenediacrylic acid (PPDA) with glycols;

bis azide resists based on poly(cis-isoprene) and bis-azides, such as 2,6-bis-(4-azidobenzal)-4-methylcyclohexanone (ABC), 4,4'-diazidostilbene, 4,4'-diazidobenzophenone and 4,4'-diazidobenzolactone; water processable azido resists;

photopolymers containing reactive binders, the binders being for example, unsaturated polymers obtained by the condensation of maleic and fumaric acid with glycols, polyfunctional acrylates and polyfunctional prepolymers;

poly(tert-butoxycarbonyloxystyrene) with an onium salt acid generator;

bis-azide-cyclized rubber compositions containing 4,4'-diazidodiphenyl sulfide and bis-azide-poly(vinyl phenol) compositions containing 3,3'-diazidodiphenyl sulfone;

poly(p-hydroxystyrene) or novolacs with melamine crosslinker together with acid catalysts, esters of poly(vinyl benzoic acid), poly(acrylic acid) and poly(methacrylic acid) having releasing groups which groups are released by heating in the presence of catalytic acid; and blocked poly-p-hydroxystyrenes.

The above mentioned examples of suitable components (b') of the instant compositions are well known in the art and are described for example in A. Reiser, Photoreactive Polymers, John Wiley & Sons, 1989.

If the above composition further contains a catalyst, the polymer structuring and pigment formation is facilitated.

Preferred are, therefore, above compositions containing additionally a catalyst (c') for positive or negative polymer structuring the resist-type resin (b'). The catalyst (c') is preferably an acid, a base or a compound selectively absorbing a specific wavelength of electromagnetic radiation, especially in the IR or NIR (near infrared, 800–2500 nm) range, and in particular, a latent acid or base.

Examples of such latent acids or bases are, for example, those capable of forming acids under actinic irradiation, such as onium salts, e.g., diazonium, sulfonium, sulfoxonium and iodonium salts, or those capable of forming bases under actinic irradiation. Particularly convenient are the latent acids and bases which are disclosed as preferred in EP 654 711.

Examples of particularly appropriate sulfonium salts are triphenylsulfonium bromide, triphenylsulfonium chloride, triphenylsulfonium iodide, triphenylsulfonium hexafluorophosphate, triphenylsulfonium hexafluoroantimonate, triphenylsulfonium hexafluoro-arsenate, triphenylsulfonium trifluoromethanesulfonate, diphenylethylsulfonium chloride, phenacyldimethylsulfonium chloride, phenacyltetrahydrothiophenium chloride, 4-nitrophenacyltetrahydrothiophenium chloride and 4-hydroxy-2-methylphenylhexahydrothiopyrylium chloride. Examples of iodonium salts are described in GB 1 539 192.

As latent acids eligible for use in the present invention, compounds which generate a slfonic acid under actinic irradiation are also appropriate. Such compounds are described, for example, in EP 166 682 and EP 085 024 as well as the literature references cited therein. Particularly preferred compounds which generate a slfonic acid under actinic irradiation are phenacyl-p-methylbenzenesulfonate, benzoin-p-toluenesulfonate, 3-(p-toluenesulfonyloxy)-2-hydroxy-2-phenyl-1-phenyl-1-propanone-(α-(p-toluenesulfonyloxy)methylbenzoin), N-(p-dodecylbenzenesulfonyloxy)-1,8-naphthalimide and N-(phenylsulfonyloxy)-1,8-naphthalimide.

Further appropriate compounds to be used as latent acids are o-nitrobenzaldehydes, which transformed to o-nitrobenzoic acid, such as 1-nitrobenzaldehyde and 2,6-dinitrobenzaldehyde; α-halogenacetophenone, such as α,α,α-trichloroacetophenone and p-tert.butyl-α,α,α-trichloroacetophenone, as well as sulfonic acid esters of o-hydroxyacetophenone, such as 2-hydroxybenzophenone methanesulfonate and 2,4-hydroxybenzophenone-bis-(methanesulfonate).

Compounds containing aromatically bound chlorine or bromine as described in EP 318 649, are finally appropriate as latent acids, too. Examples of compounds of this kind are hexafluorotetrabromo-bisphenol A, 1,1,1-tris-(3,5-dibromo-4-hydroxyphenyl)ethane and N-(2,4,6-tribromophenyl)-N'-(p-toluenesulfonyl)urea.

Preferred catalysts (c') of the instant compositions are latent acids, particularly preferred sulfonium salts.

Most preferred are triphenylsulfonium trifluoromethanesulfonate and the compounds

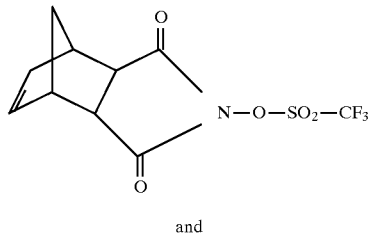

and

-continued

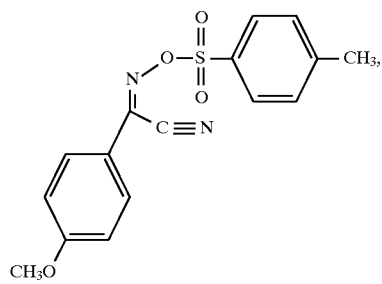

particularly triphenylsulfonium trifluoromethanesulfonate.

The compositions for forming structured colour images according to the present invention can generally be prepared simply by mixing the instant components (a'), (b') and optionally (c').

Component (a') is chosen according to the colour of the regenerated pigment particles.

The positive or negative resist-type resin, polymer or prepolymer of component (b') should be chosen according to the kind of desired colour images, i.e., positive images or negative images, and according to the treatment to be applied to the composition, such as direct heat, irradiation with electromagnetic beams, such as UV or visible light, IR, for example from a laser, or X-ray, or irradiation with particles, such as electrons or neutrons, or combinations of these treatments.

For example, if it is desired to obtain positive images by visible light irradiation, one of the positive resists as classified b'1) is chosen. If it is desired to obtain negative images by X-ray irradiation, one of the negative X-ray resists as classified b'9) is chosen. If it is desired to obtain negative images by laser irradiation, one of the heat-curable polymers, such as a mixture of methacrylic acid-methyl methacrylate copolymer and methacryloyl chloride-methyl methacrylate copolymer, contained in chemically or thermally effectable polymers as classified b'10) is chosen. In the last mentioned case, it is preferred to add, in the polymer, a compound having absorption at the wavelength of the incident laser beam so as to effectively transform optical energy into thermal energy. If it is desired to obtain negative images by applying a combination of heat and electromagnetic irradiation, then such a system as containing poly-p-hydroxystyrene with melamine crosslinker of b'10) is chosen. The choice of other resins, polymers or prepolymers, should be done likewise.

If component (c') is not added, components (a') and (b') are compounded at a ratio, by weight, of from 0.01:99.99 to 80:20, preferably from 1:99 to 70:30, more preferably from 5:95 to 60:40, and most preferably from 10:90 to 50:50.

If component (c') is added, the compounding ratio among components (a'):(b'):(c') is chosen so as to be, by weight, from 0.01:99.98:0.01 to 75:5:20, preferably from 1.00:98.90:0.10 to 70:15:15, more preferably from 5:94:1 to 60:30:10, and most preferably from 10:88:2 to 50:42:8.

The composition preferably contains the component (c').

The above prepared compositions are preferably diluted with a solvent so as to allow easy coating on a suitable substrate. Suitable solvents are the same as described above.

The composition of the present invention is diluted preferably with one or a mixture of the above solvents so that the solid content thereof is between 1 and 90% by weight, preferably between 5 and 80% by weight, more preferably between 10 and 70% by weight, and most preferably between 20 and 60% by weight, based on the solution.

The above prepared solution containing the composition of the present invention is in general applied over an appropriate substrate, subjected to electromagnetic irradiation such as visible-, UV-, laser- or X-ray irradiation, or electron- or neutron irradiation and/or heating, and optionally to development using appropriate developers.

The instant compositions are suitable for use in recording and imaging technologies, such as for example optical and thermal colour recording, colour proofing, colour copying, and particularly for manufacturing colour filters such as used in LCDs.

In another aspect of the present invention, there is provided a method for producing coloured patterns or images in which the pattern or image layer is coloured with insoluble pigment, locally regenerated from its soluble precursor, including the steps of (1) forming a polymer layer containing a soluble phthalocyanine precursor, selected from the group consisting of compounds of formulae (I) to (VII), using a composition comprising components (a'), (b') and optionally (c'), and (2) locally regenerating the pigment from the above soluble precursor by thermal or photolytic treatment.

The composition used in above step (1) is described in the foregoing text. The polymer layer formed as specified in step (1) of the above method can be a layer covering the whole surface of the substrate as well as a layer covering only certain areas of the substrate, which layer can be applied imagewise or patternwise.

One advantageous way to regenerate the pigment in step (2) is by laser marking.

As methods for forming polymer pattern or image layers, there are known various techniques like photolithography, impact printing, such as screen printing, gravure printing, flexo printing and offset printing, non-impact printing, such as ink-jet printing, thermal dye diffusion transfer, laser marking, electrodeposition etc.

In photolithography, the above composition is applied over an appropriate substrate by means of a known method, such as spin coating, spraying, dip coating or the like, followed by irradiation, for example with electromagnetic beams such as UV or visible light or X-rays, or with particles such as electrons or neutrons, and upon necessity, heat.

The kind of irradiation to be applied is chosen according to the resin, polymer or prepolymer of component (b') contained in the composition.

If the resin, polymer or prepolymer of component (b') is a positive or negative resist, then UV- or visible light is used. If the resin, polymer or prepolymer of component (b') is a positive or negative UV resist, then UV light is used.

If the resin, polymer or prepolymer of component (b') is a positive or negative X-ray resist, then X-ray is used. If the resin, polymer or prepolymer of component (b') is a positive or negative electron resist, then electron- or neutron beam is used. If the resin, polymer or prepolymer of component (b') is a photopolymerizable system, then UV- or visible light is used.

The above irradiation is carried out at a conventionally used power and dose, and if necessary, heat is applied subsequently.

The irradiation with electromagnetic beams, such as IR-, UV- or visible light or X-ray, or with beams of particles, such as electron- or neutron beams, is usually carried out through an appropriate mask or pattern so as to obtain desired structured colour images. Details of such masks or patterns are described, for example, in A. Reiser, Photoreactive Polymers, John Wiley & Sons, New York, 1989.

If laser is used as a UV- or visible light source, no mask is necessary because pattering is achieved by scanning the laser light (Direct Overwrite Technique). In impact-printing and ink-jet printing, the above composition is transferred to the substrate by screen transfer, flexo transfer, offset transfer, gravfure transfer or ink-jetting, followed irradiation. The criteria for the choice of irradiation are the same as those above. In these methods, no mask or pattern is needed since the composition is transferred to the substrate according to predetermined patterns. If necessary, heat is applied after irradiation.

In flexo printing, gravure printing and offset printing, it is also possible to transfer the composition after curing. In this method, the composition on a blanket or the like before transfer is exposed to irradiation as above and then transferred to the substrate. Since the composition is hardened in this process, polymer pattern or image layer having sharp image edges are obtained. It is preferred that the substrate is coated with an adhesive polymer so that the cured composition can easily be transferred.

In electrodeposition, the above composition is transferred by electrophoreses or micellar deposition onto the surface of patterned ITO (indium-tin-oxide) electrode formed on the surface of a substrate, followed by irradiation as above. The choice of the irradiation source is made in the same manner as above. If necessary, heat is applied afterwards.

Step (2) is carried out by applying direct heat, irradiation with electromagnetic beams, such as UV or visible light, IR, for example from a laser, or X-ray, or irradiation with particles, such as electrons or neutrons, or a combination of these treatments, to the above prepared polymer pattern or image layer. Preferably laser irradiation is used in this step (2), enabling the most preferred alternative of computer guided laser marking.

For this purpose, in step (1), a substrate is coated with the above composition using spin coating, dip coating or spray coating or the like, followed by irradiation, such as UV-, visible-, IR-, electron-, neutron- or X-ray irradiation, but without using any mask or pattern, to homogeneously cure the resin, polymer or prepolymer contained in the composition, followed by step (2) using the above laser. The choice of the appropriate irradiation is made in the same manner as described above. If necessary, heat is applied afterwards.

If the resin, polymer or prepolymer of component (b') contained in the composition is thermally curable, concomitant formation of patterns on the substrate and local regeneration of pigment from its precursor is possible for example by using a NIR laser.

It is preferred that a NIR absorber is contained in the above composition so that laser quantum energy is efficiently transformed to thermal energy.

A suitable development step may also be added, in which case conventional, well-known developers and procedures are used. This may for example be applied to the fabrication of colour filters for LCDs.

Upon irradiation with electromagnetic rays or beams of particles, or application of heat in step (2), a drastic colour change takes place while nano-sized pigment particles are generated in situ, so that formation of pigment-based structured colour images with the resolution of 0.5 $\mu$m is possible.

The above described method is of wide scope of application, and therefore, can be applied variously to optical- and thermal printing and -recording as well as the fabrication of colour filters for LCDs or the like, with higher transparency, higher contrast ratio, higher colour purity and strength, higher pattern resolution and precision of image, no (dye) colour mixing, no clogging of sieves during purification of colour/polymer mixtures, smoothness of image surface, higher registration accuracy, higher sharpness of image edges, higher thermal, chemical and light stability, and easy production of ultra thin films.

The above composition and method are appropriate for the fabrication of trichromatic colour filters for LCDs as described in EP 654 711. They are used very advantageously for the green and blue area and may be used in combination with prior art pigment precursors, such as those which generate yellow and red pigments.

In order to achieve the desired image formation, in certain applications it may not be necessary to use the aforementioned component (b') of the instant compositions. In such cases any kind of known high molecular weight organic binder material may be used as component (b"), said binder material fulfilling the function of appropriately fixing instant component (a'), the soluble pigment precursor, on the substrate on which a coloured pattern or image should be produced.

Thus, the invention further comprises also a composition for making structured colour images comprising (a') a soluble phthalocyanine precursor, selected from the group consisting of compounds of formulae (I) to (VII), and (b") a high molecular weight binder material.

Preferred binder materials (b") are polymers based on vinyl compounds, novolacs, biopolymers, polyimides, polyesters, polycarbonates, polybutyral and mixtures thereof.

There are different ways to perform step (1) of forming a polymer layer containing a soluble pigment precursor component (a'), a high molecular weight organic binder material (b") and optionally (c'). One way is for example to use a composition containing all the desired components. Another is to prepare a receiver layer containing no pigment precursor (a'), onto which the pigment precursor (a') is applied afterwards for example by ink-jetting an ink containing the pigment precursor (a') or preferably by thermal dye diffusion transfer from a donor material containing the pigment precursor (a').

Thermal dye diffusion transfer is a technology not to be confused with technologies based on mordants or chemical reactivity, where silver compounds (like in instant photography where a thermal development may be included) or colour formers (for example lactones which need a reactive partner—usually an acid or a phenol—in the receiver) are involved, though scientists still disagree on the terminology or use it improperly. A description can be found for example in Spec. Publ.—R. Soc. Chem. 133. 73–85 (1993), Proc. SPIE—Int. Soc. Opt. Eng. 1912, 252–260 (1993), Nippon Shashin Gakkaishi 55(6), 456–464 (1992), Journal of Imaging Technology 16(6), 238ff (1990) and many other publications.

The principle of thermal dye diffusion transfer is the following: a thin donor sheet (usually 1–10 μm) containing the dye is brought in contact with a receiver material, then heat is generated in a way such that the desired quantity of dye transfers to selected target areas. This can be achieved by simple heating of a broad area, but usually electronically controlled thermal array heads moving across the back surface of the donor are used. Alternatively, a high-intensity light flash (EP 391 303, EP 529 362) through a screen or a laser source (Proc. SPIE—Int. Soc. Opt. Eng. 1912, 261 ff. [1993]) can be used; preferably a laser beam focussed onto the donor is used as an energy source; in this case, preferably the donor layer contains IR dyes which convert the light into heat, and the laser is an IR laser (as in EP 529 561), so that extremely high resolutions can be obtained.

Thus, thermal dye diffusion transfer is a completely dry process totally under electronic control, leading as desired to continuous or full tone images in mosaic pixel patterns, such as needed for electronic photography printouts, color proofing and especially colour filters for LCD's.

The present soluble pigment precursors can be used in thermal dye diffusion transfer.

Accordingly, a further subject of this invention is a method for producing coloured patterns or images including the steps of (1) forming a polymer layer containing a soluble phthalocyanine precursor, selected from the group consisting of compounds of formulae (I) to (VII), a high molecular weight organic binder material (b") and optionally (c'), and (2) locally regenerating the pigment from the above soluble precursor by thermal or photolytic treatment, wherein step (1) is accomplished by:

forming a polymer layer containing the soluble pigment precursor using a composition comprising component (a') and a high molecular weight organic binder material (b") and optionally (c');

(1a) forming a polymer layer containing a high molecular weight organic binder material (b") and optionally (c'), then (1b) ink-jetting an ink comprising a pigment precursor (a') onto the polymer layer in selected target areas; or (1a) forming a polymer layer containing a high molecular weight organic binder material (b") and optionally (c'), then (1b) superposing a donor layer comprising a pigment precursor (a') and a high molecular weight organic binder material (b") onto the polymer layer, (1c) locally heating the donor layer to transfer the dye in selected target areas, and (1d) removing the donor layer from the receiver layer.

All the aforementioned embodiments described above for using instant components (a') in a method for producing coloured patterns or images also pertain to the corresponding method where components (b") are used instead of components (b').

All the aforementioned embodiments described above for using instant components (b') in a method for producing coloured patterns or images generally also pertain to the corresponding method where components (b") are used instead of components (b'), as long as the compositions of step (1) are prepared by forming a polymer layer containing dissolved pigment precursor using a composition comprising component (a') and a high molecular weight organic binder material (b") and optionally (c').

When the compositions of step (1) are prepared by ink-jetting an ink comprising a pigment precursor (a') onto a polymer layer in selected target areas, preferably the polymer layer is poly(vinyl alcohol) and the ink comprises 0.5 to 10% by weight of the pigment precursor (a') in a hydrophilic solvent; most preferably, the ink consists essentially of 1 to 5% by weight of the pigment precursor (a') in a polar solvent mixture comprising ethylene glycol or diethylene glycol.

When the compositions of step (1) are prepared by thermal dye diffusion transfer from a donor layer comprising a pigment precursor (a') onto a polymer layer in selected target areas, preferably the receiver polymer layer is polyester, poly(vinyl chloride/vinyl acetate), polycarbonate or a mixture thereof, and the donor layer contains 1 to 10% by weight of the pigment precursor (a') in a different binder; most preferably, the receiver polymer layer is coated as a 10 to 20% by weight solution and contains 0.1 to 5% by weight of surfactants, and the donor's binder consists essentially of polybutyral or cellulose derivatives. Further details concerning the donor's and receiver's preferred chemical compositions are well-known to specialists and are subject of many patents and other publications (such as in EP 507 734 and EP 508 954). The donor may be re-used many times, and the relative motion of donor and receiver may be varied, for example in order to increase the colour intensity. Usually, the donor is just peeled off after the transfer step, but it may be useful in some cases to remove it partially or totally by chemical dissolution.

Polymeric layers containing dissolved pigment precursor components (a'), high molecular weight organic binder materials (b") and optionally (c') have similar properties as positive or negative resist-type resins, polymers or prepolymers (b') after structuration and may be used in replacement of them.

The above composition and method are also appropriate for the fabrication of trichromatic colour filters for LCDs as described for resists, advantageously for the green and blue area.

The invention is illustrated in more detail by the following examples.

EXAMPLE 1

[in analogy to F. Baumann, U.S. Pat. No. 2,683,643, Example 89]: 12 g copper phthalocyanine, 36 g bromine, 12 g pyridine and 200 g methanol are heated to reflux for 40 min. under stirring in a 500 ml flask inertized with argon. Brown crystals form rapidly. The mixture is cooled to 25° C. and filtered. The residue is washed twice with 50 ml of methanol each and once with 50 ml of diethylether, then dried for 4 hours at 50° C./160 mbar. 16.52 g of brown crystals of following elemental composition are obtained: 45.63% C, 2.73% H, 12.56% N, 28.36% Br. The thermogravimetric analysis (TGA, 10° C./min) shows a decomposition starting at 130° C., with a peak temperature of 153° C. and a weight loss of 26.1%. The TGA residue shows the characteristical IR absorption peaks of copper phthalocyanine.

10 g of the above brown crystals are suspended in 22 g of toluene in a 100 ml flask equipped for gas introduction unter level. For 45 min., $NH_3$ gas is then passed through the suspension, the temperature of which rises to 45° C. before decreasing again to room temperature. The reaction mixture is filtered and the residue rinsed with toluene until colorless. The filtrate is evaporated and the brown residue is thoroughly washed with 50 ml of n-pentane in 3 portions and dried for 1 hour at 60° C./160 mbar. 1.28 g of brown crystals of following elemental composition are obtained: 61.84% C, 3.64% H, 16.28% N, 4.94% Br. The raw product is very soluble in most organic solvents. The TGA shows a decomposition starting at 100° C., with a peak temperature of 181° C. and a weight loss of 20.2%. The TGA residue shows the characteristical IR absorption peaks of copper phthalocyanine.

A sample of the raw product is purified by chromatography on silica gel with ethyl acetate as eluent, in order to eliminate traces of polar impurities. One gets a brown product, identifiable by thin layer chromatography (TLC) as a mixture of methoxy/methoxy and bromo/methoxy dihydro copper phthalocyanine of following elemental composition: 62.06% C, 3.75% H, 16.03% N, 4.94% Br. The TGA shows a decomposition starting at 110° C., with a peak temperature at 170° C. and a weight loss of 22.6%.

EXAMPLE 2

[in analogy to F. Baumann, Angew. Chem. 68/142 (1956), compound LIIIa]: 25.6 ml of pyridine is added to a solution of 0.46 g (0.02 mol) of sodium in 3 ml of methanol under stirring in an argon atmosphere. 5.12 g (0.04 mol) of phthalodinitrile are then added in portions (slightly exothermic reaction). After stirring the yellowish orange solution for 2 hours, a solution of 1.35 g (0.01 mol) copper dichloride in 13 ml of methanol is added. 1.7 g (0.02 mol) of piperidine are then added dropwise to the brown suspension, which is further stirred overnight. The methanol is then evaporated, the mixture is filtrated and the residue is washed with pyridine, toluene, hexane and water and dried at the air, lefting 3.1 g (42%) of green powder which are then extracted with chloroform in a Soxhlet apparatus for 6 hours. The chloroform solution is then evaporated and the brown residue is washed with hexane and dried. The product is dipiperidino dihydro copper phthalocyanine as shown by the elemental composition: 66.78% C, 4.98% H, 17.78% N (calc. for $C_{42}H_{36}N_{10}Cu$: 67.77% C, 4.88% H, 18.82% N). IR: 722, 1392, 1458, 1492 and 2912 $cm^{-1}$ (KBr); MS: 744 ($M^+$); UV/Vis: $\lambda_{max}(CHCl_3)$: 405, 337. The solubility in xylene is 0.9 g/100 ml. The TGA shows a decomposition with an average temperature of 236° C. and a weight loss of 22.6%, corresponding to the splitting of 2 piperidino groups. The TGA residue shows the characteristical spectroscopic properties of pure copper phthalocyanine.

EXAMPLE 3

25.6 ml of pyridine is added to a solution of 0.46 g (0.02 mol) of sodium in 3 ml of methanol under stirring in an argon atmosphere. 5.12 g (0.04 mol) of phthalodinitrile are then added in portions (slightly exothermic reaction). After 2 hours of additional stirring, a solution of 1.35 g (0.01 mol) copper dichloride in 13 ml of methanol is added to the yellowish orange solution. 2.54 g (0.02 mol) of 4-n-propyl-piperidine are then added dropwise to the brown suspension, which is further stirred overnight. The mixture is then filtrated and the residue is washed with pyridine, toluene, hexane and water and dried at the air, lefting 2.4 g (29%) of green powder which are extracted with chloroform in a Soxhlet apparatus for 6 hours. The chloroform solution is then evaporated and the brown residue washed with hexane and dried. The product is di-(4-n-propyl)-piperidino dihydro copper phthalocyanine as shown by the elemental composition: 69.08% C, 5.96% H, 16.40% N; (calc. for $C_{48}H_{48}N_{10}Cu$: 69.59% C, 5.84% H, 16.91% N). IR: 720, 1400, 1456, 1492, 1530 and 2924 $cm^{-1}$ (KBr); MS: 828 ($M^+$); UV/V: $\lambda_{max}(CHCl_3)$: 405, 337. The solubility in xylene is 2.3 g/100 ml. The TGA shows a decomposition with an average temperature of 225° C. and a weight loss of 29%, corresponding to the splitting of two 4-n-propyl-piperidino groups. The TGA residue shows the characteristical IR absorption bands of pure copper phthalocyanine.

EXAMPLE 4

A 16% solution of the product of example 3 in chloroform is spin-coated onto a glass disc at 2'500 rpm. The pale yellowish disc is dried at 100° C. for 2 min, then heated at 240° C. for 3 min. The characteristic blue colour of copper phthalocyanine appears. The presence of copper phthalocyanine is confirmed by UV/VIS spectroscopy.

EXAMPLE 5

A solution of 50 mg of the product of example 2, 250 mg of p-hydroxy-polystyrene ®PHM-C (Maruzen) and 59 mg of ®Cymel 303 (American Cyanamid) in 1 ml of dioxane is spin-coated onto a glass disc at 2'500 rpm. The pale yellowish disc is dried at 100° C. for 1 min, then heated at 240° C. for 2 min. The characteristic blue colour of copper phthalocyanine appears. The presence of copper phthalocyanine is confirmed by UV/VIS spectroscopy.

EXAMPLE 6

A solution of 50 mg of the product of example 2, 250 mg of p-hydroxy-poly-styrene ®PHM-C (Maruzen) and 59 mg of ®Cymel 303 (American Cyanamid) in 1 ml of dioxane is spin-coated onto a glass disc at 2'500 rpm. The pale yellowish disc has an absorbance of 1.19 at $\lambda_{max}$=315 nm after drying at 100° C. for 1 min. After heating at 200° C. for 15 min, whereupon the characteristic blue colour of copper phthalocyanine appears, the absorbance is 1.22 at $\lambda_{max}$=612 nm. Upon additional heating, the absorbance decreases only insignificantly, demonstrating the outstanding thermal stability which can be obtained with the present compositions.

EXAMPLE 7

A solution of 100 mg of the product of example 3, 250 mg of p-hydroxy-polystyrene ®PHM-C (Maruzen) and 59 mg of ®Cymel 303 (American Cyanamid) in 1 ml of dioxane is spin-coated onto a glass disc at 2'500 rpm. The pale yellowish disc has an absorbance of 1.90 at $\lambda_{max}$=315 nm after drying at 100° C. for 1 min. After heating at 200° C. for 15 min, whereupon the characteristic blue colour of copper phthalocyanine appears, the absorbance is 1.86 at $\lambda_{max}$=610 nm. Upon additional heating, the absorbance decreases only insignificantly, demonstrating the outstanding thermal stability which can be obtained with the present compositions.

EXAMPLE 8

The product of example 2 is recrystallised from chloroform so as to obtain single crystals. From the X-ray analysis of one such single crystal, the following structure (IIIA) in accordance with formula (III) can be assigned:

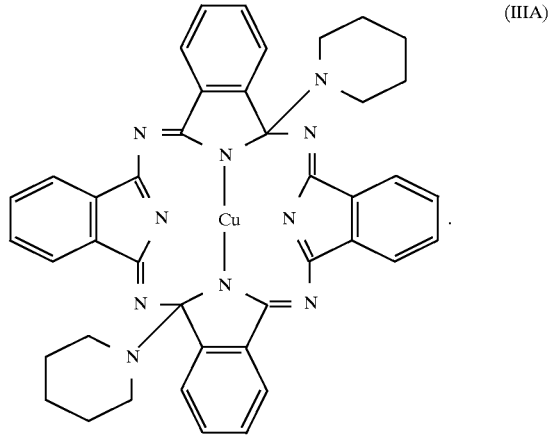

(IIIA)

EXAMPLE 9

25.6 ml of pyridine is added to a solution of 0.46 g (0.02 mol) of sodium in 3 ml of methanol under stirring in an argon atmosphere. 5.12 g (0.04 mol) of phthalodinitrile are then added in portions (slightly exothermic reaction). After stirring the yellowish orange solution for 2 hours, a solution of 1.35 g (0.01 mol) copper dichloride in 13 ml of methanol is added. After stirring overnight, the solvent in evaporated under reduced pressure. 1.74 g (0.02 mol) of morpholine are then added dropwise, and the mixture is stirred overnight. The brown suspension is then filtrated and the residue is washed with pyridine, toluene, hexane and water and dried at the air. The resulting powder is then extracted with chloroform in a Soxhlet apparatus for 6 hours, which treatment eliminates traces of insoluble unreacted copper phthalocyanine. The chloroform solution is then evaporated under reduced pressure and the brown residue is washed with hexane and dried. The product (0.60 g, 8% of theory) is dimorpholino dihydro copper phthalocyanine as shown by the elemental composition: 64.45% C, 4.51% H, 16.77% N (calc. for $C_{40}H_{32}N_{10}O_2Cu$: 64.20% C, 4.31% H, 18.72% N). IR: 722, 1398, 1456, 1490, 1525 and 2960 cm$^{-1}$ (KBr); MS: 748 (M$^{+1}$); UV/Vis: $\lambda_{max}$(CHCl$_3$): 405, 337. The TGA shows a decomposition with an average temperature of 209° C. and a weight loss of 20.6%, corresponding to the splitting of 2 morpholino groups. The TGA residue shows the characteristical spectroscopic properties of pure copper phthalocyanine.

EXAMPLE 10

A solution is prepared by heating 250 mg of ®PHM-C (Maruzen) and 59 mg of ®Cymel 300 (American Cyanamid) in 1 ml of dioxane. 100 mg of the product of example 9 are then added, and the solution is filtered at room temperature through a 0,45 μm ®Teflon filter and spin-coated onto a KBr disc at 1'000 rpm. The pale brownish disc is dryed at 100° C., then heated to 200° C., whereupon the characteristic blue colour of copper phthalocyanine appears. The polymer layer is detached by treatment with water, placed on a piece of polycarbonate filter and embedded in ®Araldite resin. 100 nm thin slices are cut, which are examined by electron microscopy (40'000×magnification). The vast majority of particles have round shapes with a maximum diameter of 6 to 26 nm.

EXAMPLE 11

25.6 ml of pyridine is added to a solution of 0.46 g (0.02 mol) of sodium in 3 ml of methanol under stirring in an argon atmosphere. 5.12 g (0.04 mol) of phthalodinitrile are then added in portions (slightly exothermic reaction). After stirring the yellowish orange solution for 2 hours, a solution of 1.35 g (0.01 mol) zinc dichloride in 13 ml of methanol is added. After stirring overnight, the solvent in evaporated under reduced pressure. 1.74 g (0.02 mol) of morpholine are then added dropwise, and the mixture is stirred overnight. The brown suspension is then filtrated and the residue is washed with pyridine, toluene, acetone, water and acetone, and dried at the air. The resulting slightly greenish powder (2.5 g) is then extracted with chloroform in a Soxhlet apparatus for 6 hours, which treatment eliminates traces of insoluble unreacted zinc phthalocyanine. The chloroform solution is then evaporated under reduced pressure and the greenish white residue is washed with hexane and dried. The product (2.38 g, 31.7% of theory) is dimorpholino dihydro zinc phthalocyanine as shown by the elemental composition: 59.81 % C, 4.24% H, 15.41 % N (calc. for $C_{40}H_{32}N_{10}O_2Zn$: 64.05% C, 4.30% H, 18.67% N). IR: 720, 1060, 1230, 1300, 1398, 1460, 1495, 1525, 2820 and 2960 cm$^{-1}$ (KBr). The TGA shows a decomposition with an average temperature of 228° C. and a weight loss of 22.3%, corresponding to the splitting of 2 morpholino groups. The TGA residue shows the characteristical spectroscopic properties of pure zinc phthalocyanine.

EXAMPLE 12

25.6 ml of pyridine is added to a solution of 0.46 g (0.02 mol) of sodium in 3 ml of methanol under stirring in an argon atmosphere. 5.12 g (0.04 mol) of phthalodinitrile are then added in portions (slightly exothermic reaction). After stirring the yellowish orange solution for 2 hours, a solution of 1.35 g (0.01 mol) copper dichloride in 13 ml of methanol is added. After stirring overnight, the solvent in evaporated under reduced pressure. 1.74 g (0.02 mol) of pyrrolidine are then added dropwise, and the mixture is stirred overnight. The brown suspension is then filtrated and the residue is washed with pyridine, toluene, hexane and water and dried at the air. The resulting powder is then extracted with chloroform in a Soxhlet apparatus for 6 hours, which treatment eliminates traces of insoluble unreacted copper phthalocyanine. The chloroform solution is then evaporated under reduced pressure and the brown residue is washed with hexane and dried. The product (0.82 g, 11.4% of theory) is dipyrrolidino dihydro copper phthalocyanine as shown by the elemental composition: 66.13% C, 4.78% H, 18.44% N (calc. for $C_{40}H_{32}N_{10}Cu$: 67.07% C, 4.50% H, 19.55% N). IR: 722, 1398, 1456, 1490, 1525 and 2960 cm$^{-1}$ (KBr); MS: 716 (M$^+$); UV/Vis: $\lambda_{max}$(CHCl$_3$): 405, 337. The TGA shows a decomposition with an average temperature of 198° C. and a weight loss of 20.6%, corresponding to the splitting of 2 pyrrolidino groups. The TGA residue shows the characteristical spectroscopic properties of pure copper phthalocyanine.

EXAMPLE 13

25.6 ml of pyridine is added to a solution of 0.46 g (0.02 mol) of sodium in 3 ml of methanol under stirring in an argon atmosphere. 5.12 g (0.04 mol) of phthalodinitrile are then added in portions (slightly exothermic reaction). After stirring the yellowish orange solution for 2 hours, a solution of 2.38 g (0.01 mol) nickel dichloride in 13 ml of methanol is added. After stirring overnight, the solvent in evaporated under reduced pressure. 1.7 g (0.02 mol) of piperidine are then added dropwise, and the mixture is stirred overnight. The suspension is then filtrated and the residue is washed with pyridine, toluene, hexane and water and dried at the air. The resulting powder is then extracted with chloroform in a Soxhlet apparatus for 6 hours, which treatment eliminates traces of insoluble unreacted nickel phthalocyanine. The chloroform solution is then evaporated under reduced pressure and the brown residue is washed with hexane and dried. The brown product (0.45 g, 6.0% of theory) is dipyrrolidino dihydro nickel phthalocyanine as shown by the elemental composition: 66.13% C, 4.78% H, 18.44% N (calc. for $C_{42}H_{36}N_{10}Ni$: 68.21% C, 4.91% H, 18.94% N). IR: 730, 1404, 1459, 1492, 1540 and 2926 cm$^{-1}$ (KBr); MS: 739 (M$^+$); UV/Vis: $\lambda_{max}$(CHCl$_3$): 478, 326. The TGA shows a decomposition with an average temperature of 198° C. and a weight loss of 23.3%, corresponding to the splitting of 2 piperidino groups. The TGA residue shows the characteristical spectroscopic properties of pure nickel phthalocyanine.

EXAMPLE 14

7 ml of pyridine is added to a solution of 0.12 g (0.005 mol) of sodium in 4 ml of methanol under stirring in an argon atmosphere. 2.0 g (0.01 mol) of 3,4-dichloro-phthalodinitrile are then added in portions (slightly exothermic reaction). After stirring the yellowish orange solution for 2 hours, a solution of 0.34 g (0.0025 mol) copper dichloride in 3 ml of methanol is added. After stirring overnight, the solvent in evaporated under reduced pressure. 0.43 9 (0.005 mol) of piperidine are then added dropwise, and the mixture is stirred overnight. The brown suspension is then filtrated and the residue is washed with pyridine, toluene, hexane and water, and dried at the air. The resulting powder is then extracted with chloroform in a Soxhlet apparatus for 6 hours, which treatment eliminates traces of insoluble unreacted copper phthalocyanine. The chloroform solution is then evaporated under reduced pressure and the residue is washed with hexane and dried. The brown product (0.092 g, 3.5% of theory) is dipiperidino-dihydro-2,3,9,10,16,17,22,23-octachloro copper phthalocyanine. UV/Vis: $\lambda_{max}$(CHCl$_3$): 405, 337. The TGA shows a decomposition with an average temperature of 177° C. and a weight loss of 14%, corresponding to the splitting of 2 piperidino groups. The TGA residue shows the characteristical spectroscopic properties of pure 2,3,9,10,16,17,22,23-octachloro copper phthalocyanine.

EXAMPLE 15

A solution of 0.14 g (0.0058 mol) of sodium in 1 ml of methanol is added under stirring in an argon atmosphere to a suspension of 2.0 g (0.0029 mol) methoxy/bromo dihydro copper phthalocyanine, which was obtained by purification of the product of example 1, in 20 ml of dioxane. The greenish suspension is stirred overnight and then filtrated. The residue is washed with dioxane and dried at the air. The resulting powder is then extracted with chloroform in a Soxhlet apparatus for 6 hours. The chloroform solution is then evaporated under reduced pressure and the residue is washed with hexane and dried. The brown product (0.270 g, 14.6% of theory) is dimethoxy dihydro copper phthalocyanine. The TGA shows a decomposition with an average temperature of 224° C. and a weight loss of 12%, corresponding to the splitting of 2 methoxy groups. The TGA residue shows the characteristical spectroscopic properties of pure copper phthalocyanine.

EXAMPLE 16

A solution of 0.14 g (0.0058 mol) of sodium in 1 ml of 1-octanol is added under stirring in an argon atmosphere to a suspension of 2.0 g (0.0029 mol) methoxy/bromo dihydro copper phthalocyanine, which was obtained by purification of the product of example 1, in 20 ml of dioxane. The greenish suspension is stirred overnight and then filtrated. The residue is washed with dioxane, and the combined filtrates are evaporated under reduced pressure and dried at the air. The residue is suspended in hexane, filtered and dried. The beige-brown product (0.50 g, 23% of theory) is dioctyloxy dihydro copper phthalocyanine. The TGA shows a decomposition with an average temperature of 175° C. and a weight loss of 33%, corresponding to the splitting of 2 octyloxy groups. The TGA residue shows the characteristical spectroscopic properties of pure copper phthalocyanine.

EXAMPLE 17

A formulation is prepared by dissolving 450 mg of a copolymer of methacrylic acid and benzylmethacrylate ($M_n$=8500, $M_w$=35000; obtained by free radical induced polymerization of the corresponding monomers with AIBN in toluene for 20 hours at 70° C.), 150 mg dipentaerythritol-monohydroxy-pentaacrylate (®SR 399 from Sartomer Inc.), 5 mg ®Irgacure 369 (Ciba-Geigy Ltd.), 1 mg dimethylaminopyridine and 90 mg of the phthalocyanine precursor of example 3 in 4 ml dioxane. The thus obtained formulation is spin-coated at 1000 rpm ontop of a 7.5×7.5 cm Corning 7059 type glass substrate and subsequently dried on a hot-plate for 60 seconds at 60° C., yielding a film which has a thickness of 1.3 μm. The sample plate is then exposed for 300 seconds through a chrome/quartz mask by using a 500

Watt ®Ushio UXM-502 MD exposure tool, baked on the hotplate for 3 minutes at 60° C. and developed for 30 seconds in an aqueous solution of tetramethyl ammonium hydroxide (0.262 mol/l). Finally the plate is baked on the hotplate for 1 minute at 250° C. The net result is the generation of transparent, non-turbid blue micropatterns, which represent a negative image of the mask, ontop of the glass substrate.

EXAMPLE 18

The procedure of example 17 is repeated, with the difference that the exposure is performed by using a 364 nm argon laser (0.30 nW, distance 85 mm) and scanning lines at an irradiation speed of 0.6 mm²/s instead of exposing through a mask. A grid with a very high resolution is obtained.

EXAMPLE 19

The procedure of example 17 is repeated, but instead of the phthalocyanine precursor the different precursor LPY 139 was used.

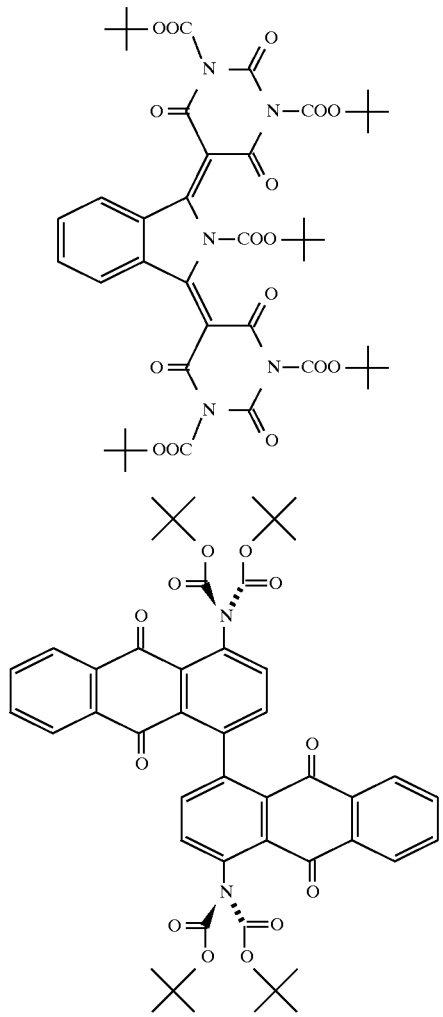

After development, the colorless and yellow image is subjected again to the procedure of example 17, this time using LPR 177 instead of LPY 139. After the second development, the colorless, yellow and red image is subjected again to the procedure of example 17, this time using the same phthalocyanine precursor as in Example 17.

A yellow, red and blue transparent image having excellent properties is obtained, which can be used as a trichromatic colour filter.

EXAMPLE 20

The sample of example 19 is used as a color filter in an electronic display, showing excellent saturation, hue, transparency and light fastness.

We claim:

1. A process for the colouration of high molecular weight organic materials in the mass, wherein a soluble phthalocyanine precursor, selected from the group consisting of compounds of formulae (I) to (VII),

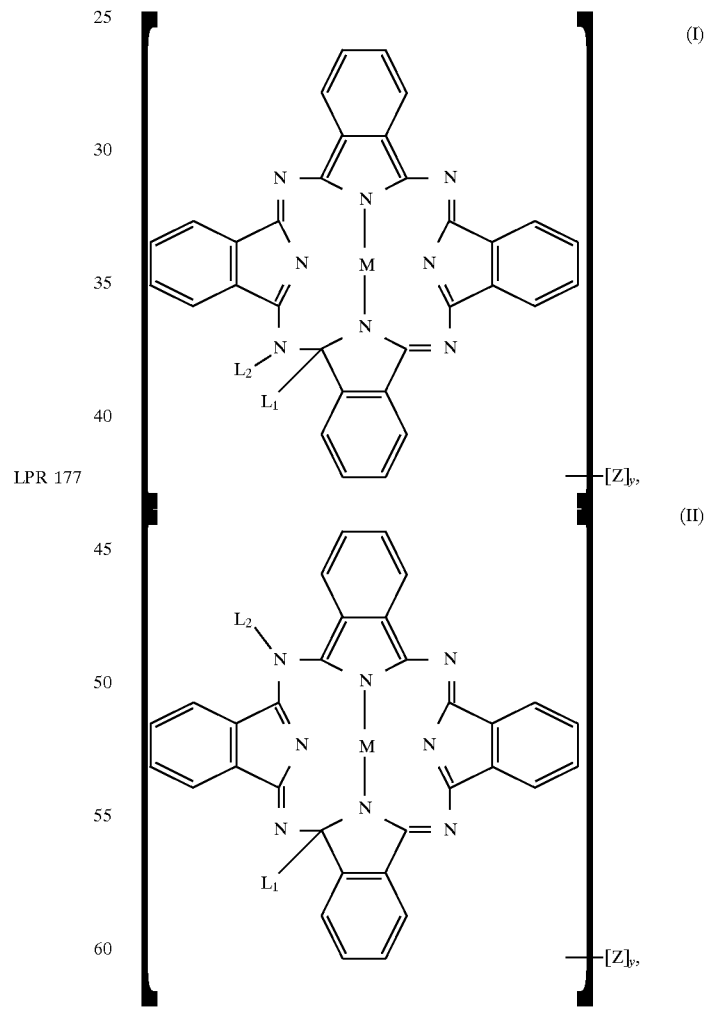

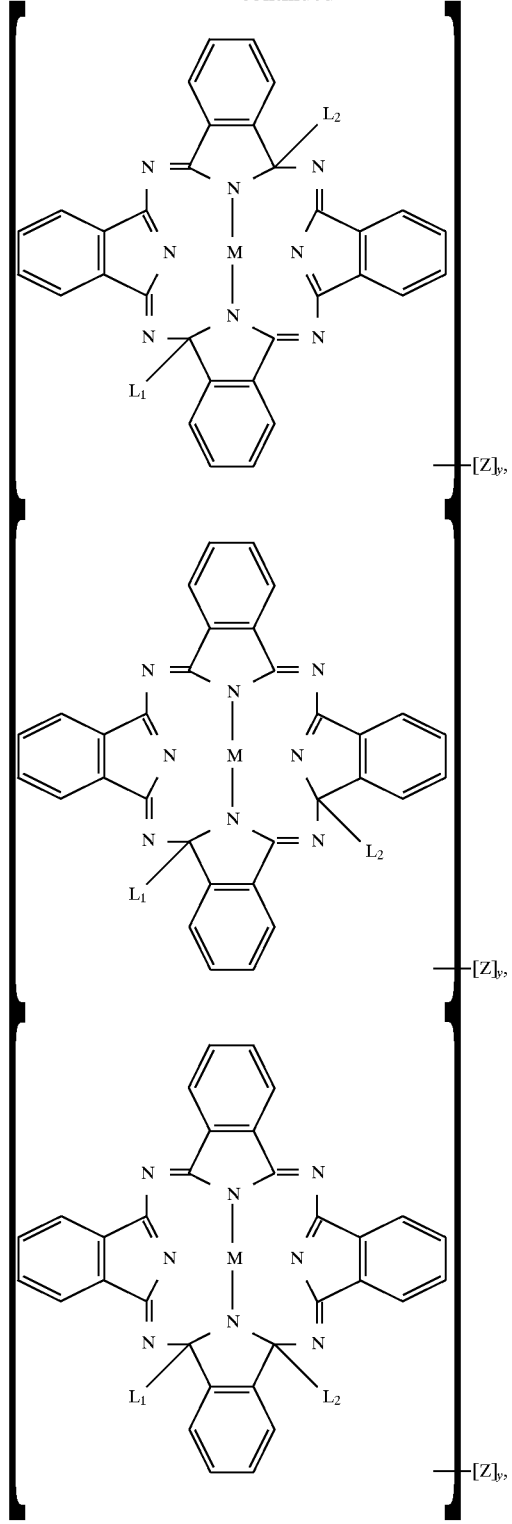

(III)

(IV)

(V)

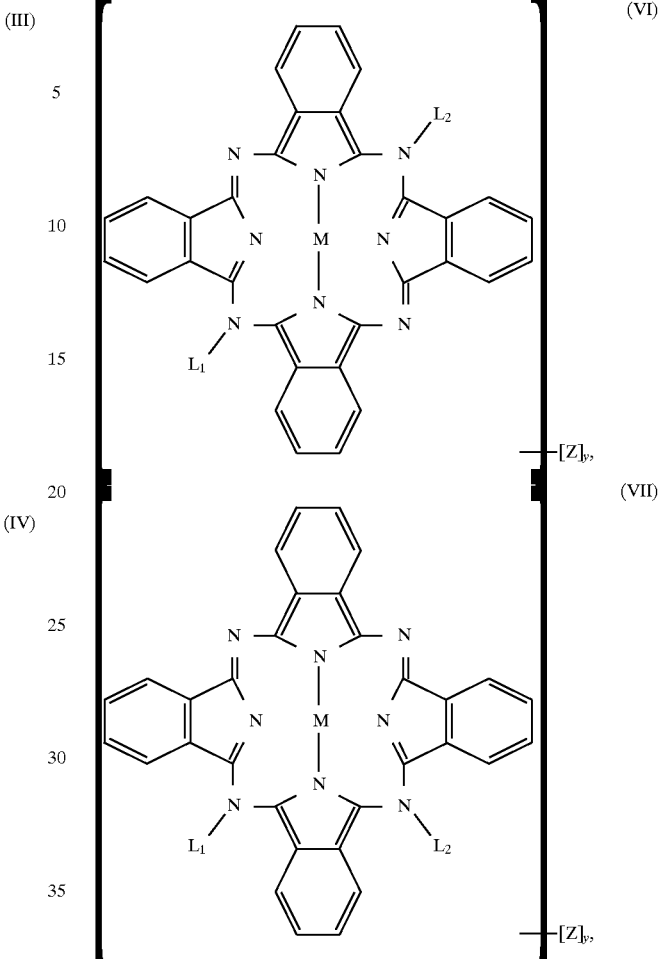

(VI)

(VII)

wherein $L_1$ and $L_2$ are independently from each other $C_1$–$C_{18}$alkoxy, $C_1$–$C_{18}$alkylthio, $C_1$–$C_{18}$alkyl-amino, $C_2$–$C_{18}$dialkylamino, or an unsubstituted or with 1 or 2 $C_1$–$C_{12}$alkyl groups substituted 5- or 6-membered imino ring which contains zero or one additional nitrogen or oxygen atom, M is two hydrogens, two metals with one valence or a metal with two or more valences, y is a number from 0 to 16 and each Z is bound to a peripheral position of the phenyl rings and is, independently of the other halogen, $C_1$–$C_{18}$alkyl, $C_1$–$C_{18}$alkoxy, $C_1$–$C_{18}$alkylthio or $C_2$–$C_{18}$dialkylamino, is added to the high molecular weight material, and wherein said high weight organic material containing a compound of formula (I) to (VII) in the mass is heated to at least 130° C., or is exposed to a radiation of wavelength 250–500 nm, whereby said compound of formula (I) to (VII) is converted, essentially in the absence of water, into a compound of formula (VIII)

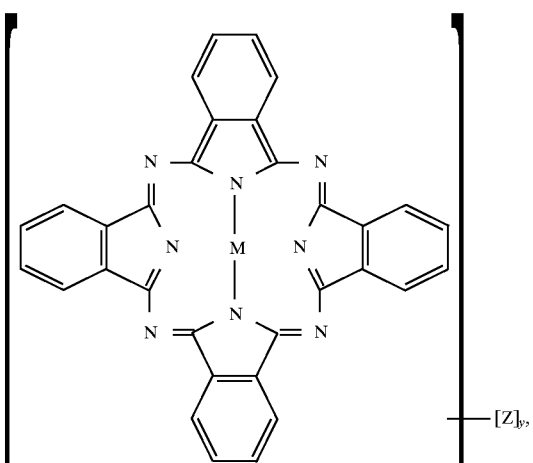

(VIII)

—[Z]$_{y'}$ wherein M, y and Z have the same meaning as above.

2. A process of claim 1, wherein $L_1$ and $L_2$ are $C_2$–$C_{18}$dialkylamino, morpholino, pyrrolidino or unsubstituted or with $C_1$–$C_{12}$alkyl substituted piperidino.

3. A process of claim 1, wherein M is $H_2$, Zn, Cu, Ni, Fe, Ti or V.

4. A process of claim 1, wherein Z is bromo or chloro.

5. A process of claim 1, wherein the conversion to a compound of formula (VIII) is achieved in the absence of any compound which is caustic or reactive with the precursor of formula (I) to (VII), with the pigment of formula (VIII) or with the high molecular weight organic material upon heating to 130°–400° C. or upon exposure to light of wavelength 250–500 nm.

6. A process of claim 1, wherein heating is achieved by an IR laser, the wavelength of which is in the range 800–10600 nm.

7. A process of claim 1, wherein 0.01 to 70% by weight of the soluble phthalocyanine precursor is used, based on the high molecular weight organic material to be pigmented.

8. A composition comprising
   (a) a soluble phthalocyanine precursor, selected from the group consisting of compounds of formulae (I) to (VII),

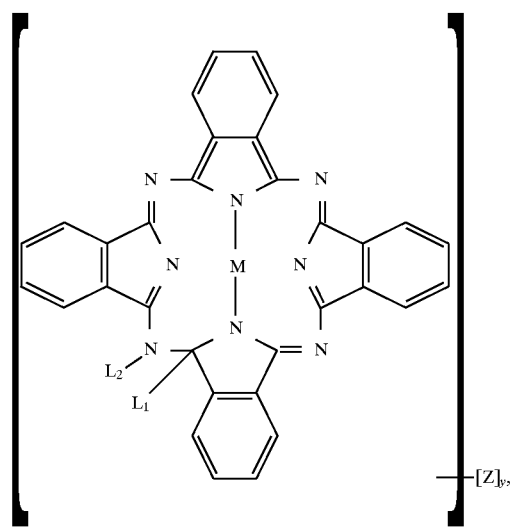

(I)

—[Z]$_{y'}$

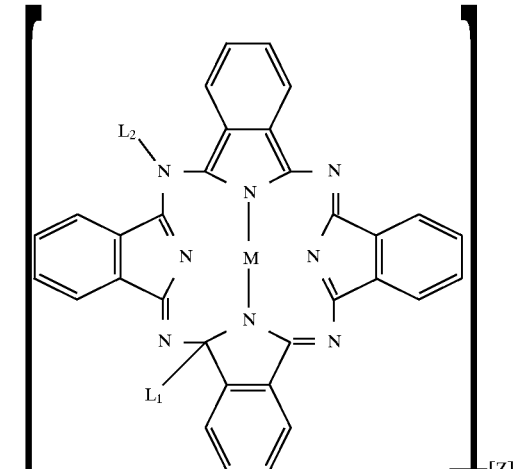

(II)

—[Z]$_{y'}$

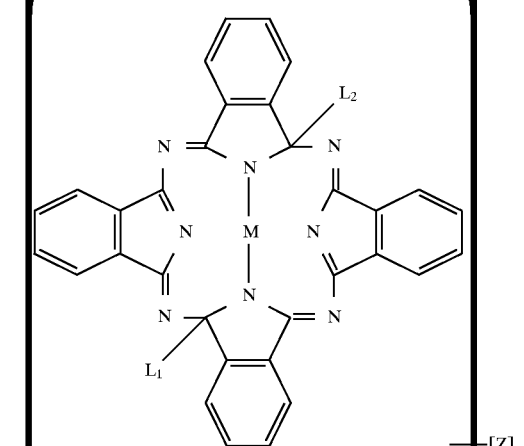

(III)

—[Z]$_{y'}$

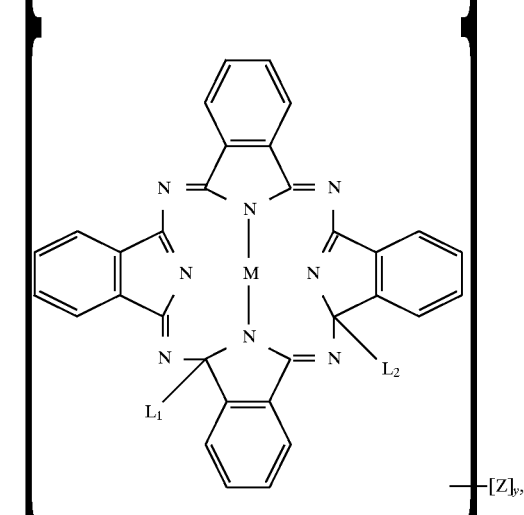

(IV)

—[Z]$_{y'}$

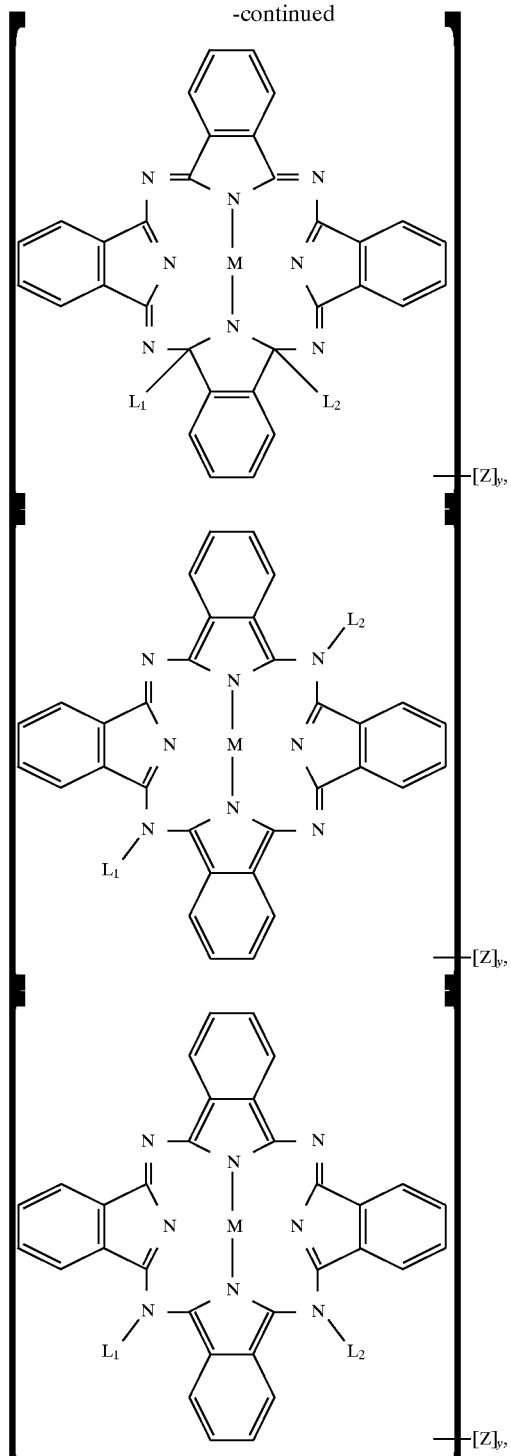

wherein $L_1$ and $L_2$ are independently from each other $C_1$–$C_{18}$alkoxy, $C_1$–$C_{18}$alkylthio, $C_1$–$C_{18}$alkylamino, $C_2$–$C_{18}$dialkylamino, or an unsubstituted or with 1 or 2 $C_1$–$C_{12}$alkyl groups substituted 5- or 6-membered imino ring which contains zero or one additional nitrogen or oxygen atom, M is two hydrogens, two metals with one valence or a metal with two or more valences, y is a number from 0 to 16, and each Z is bound to a peripheral position of the phenyl rings and is, independently of the other halogen, $C_1$–$C_{18}$alkyl, $C_1$–$C_{18}$alkoxy, $C_1$–$C_{18}$alkylthio or $C_2$–$C_{18}$dialkylamino, and (b) a high molecular weight organic material which is essentially impermeable to water and aqueous solvents, wherein said soluble phthalocyanine precursor (a) is embedded in the mass of said high molecular weight organic material (b).

9. A composition of claim 8, wherein the high molecular weight organic material (b) absorbs ≦3% by weight of water and aqueous solvents and does not swell in water.

10. A composition of claim 8, wherein the soluble phthalocyanine precursor (a) is contained in amounts of 0.01 to 70% by weight, based on the high molecular weight organic material (b) to be pigmented.

11. A composition obtained by the method of claim 1, wherein the single phthalocyanine pigment particles of formula (VIII) have a length ≦1 μm and are essentially not aggregated.

12. A process of claim 1, wherein $L_1$ and $L_2$ are independently from each other $C_1$–$C_{18}$alkylthio, $C_1$–$C_{18}$alkylamino, $C_2$–$C_{18}$dialkylamino, or an unsubstituted or with 1 or 2 $C_1$–$C_{18}$alkyl groups substituted 5- or 6-membered imino ring which contains zero or one additional nitrogen or oxygen atom.

13. A composition for making structured colour images comprising (a') a soluble phthalocyanine precursor, selected from the group consisting of compounds of formulae (I) to (VII),

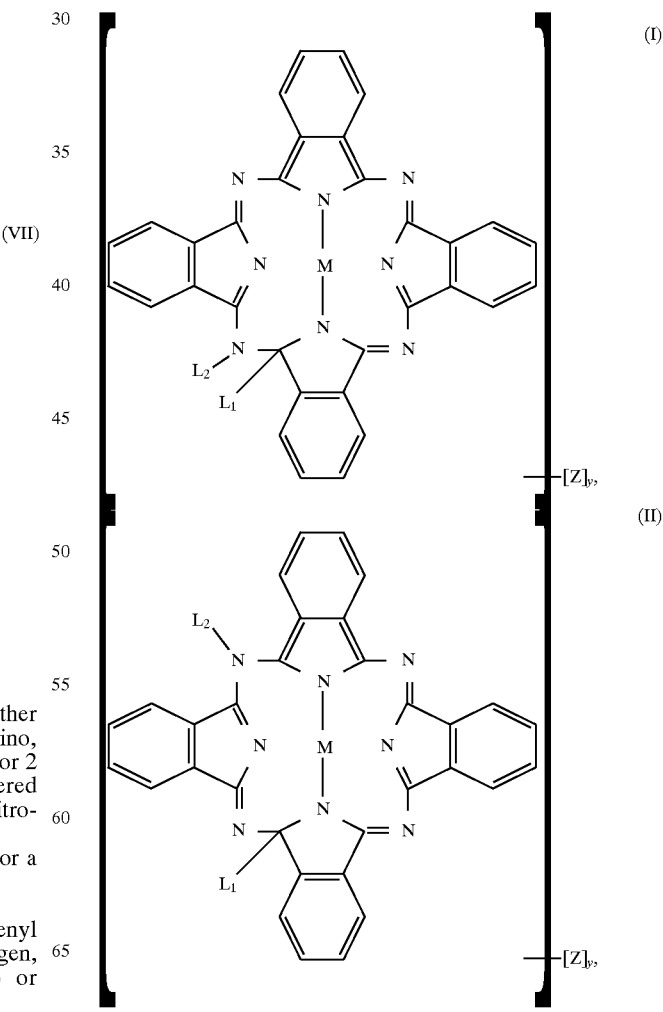

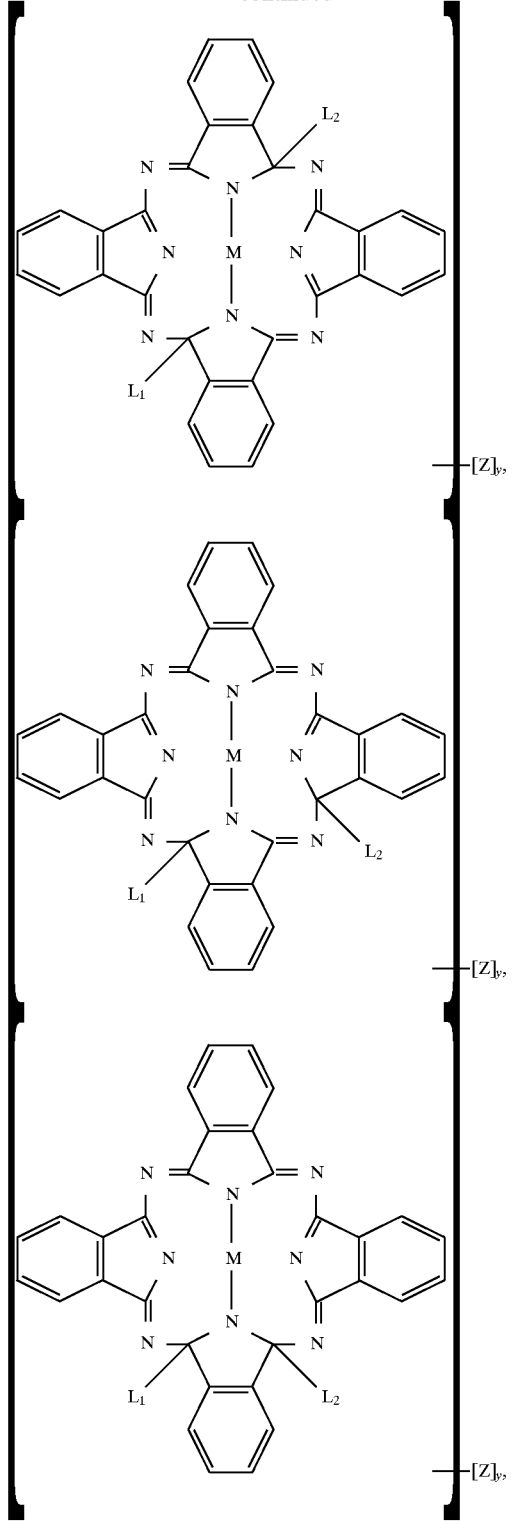

(III)

(IV)

(V)

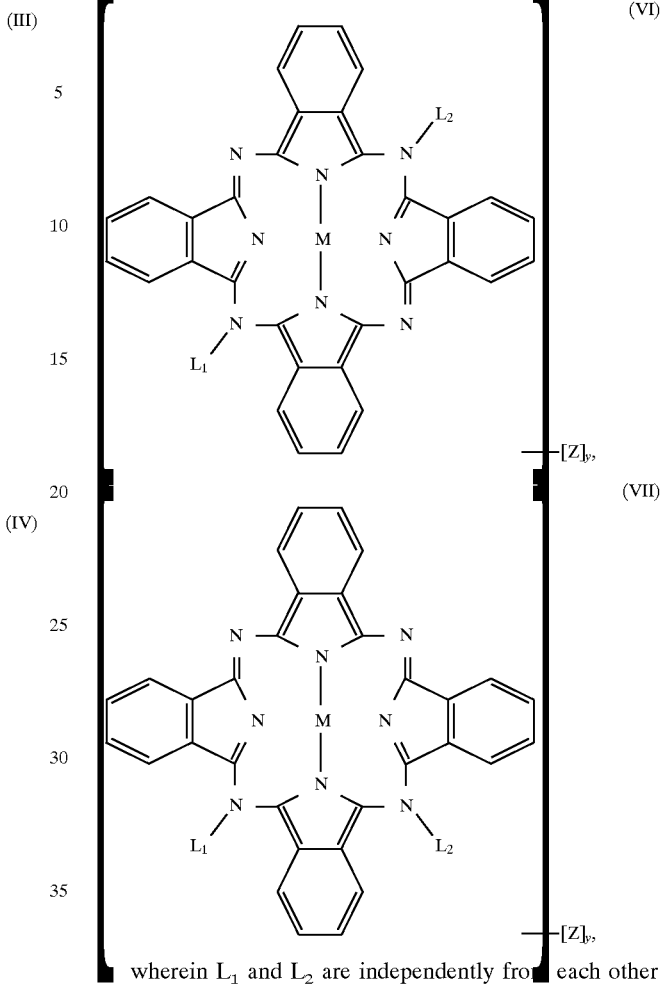

(VI)

(VII)

wherein $L_1$ and $L_2$ are independently from each other $C_1$–$C_{18}$alkoxy, $C_1$–$C_{18}$alkylthio, $C_1$–$C_{18}$alkylamino, $C_2$–$C_{18}$dialkylamino, or an unsubstituted or with 1 or 2 $C_1$–$C_{12}$alkyl groups substituted 5- or 6-membered imino ring which contains zero or one additional nitrogen or oxygen atom, M is two hydrogens, two metals with one valence or a metal with two or more valences, y is a number from 0 to 16, and each Z is bound to a peripheral position of the phenyl rings and is, independently of the other halogen, $C_1$–$C_{18}$alkyl, $C_1$–$C_{18}$alkoxy, $C_1$–$C_{18}$alkylthio or $C_2$–$C_{18}$dialkylamino, and (b') a positive or negative resist resin, polymer or prepolymer which can be structured by crosslinking, polymerisation or depolymerization by applying heat or by irradiation.

14. A composition of claim 13, containing additionally a catalyst (c') for positive or negative polymer structuring the resist-type resin (b').

15. A composition of claim 14, wherein the compounding ratio among components (a'):(b'):(c') is from 0.01:99.98:0.01 to 75:5:20 by weight.

16. A method for producing coloured patterns or images in which the pattern or image layer is coloured with insoluble pigment, locally regenerated from its soluble precursor, including the steps of
(1) forming a polymer layer containing a soluble phthalocyanine precursor, selected from the group consisting of compounds of formulae (I) to (VII),
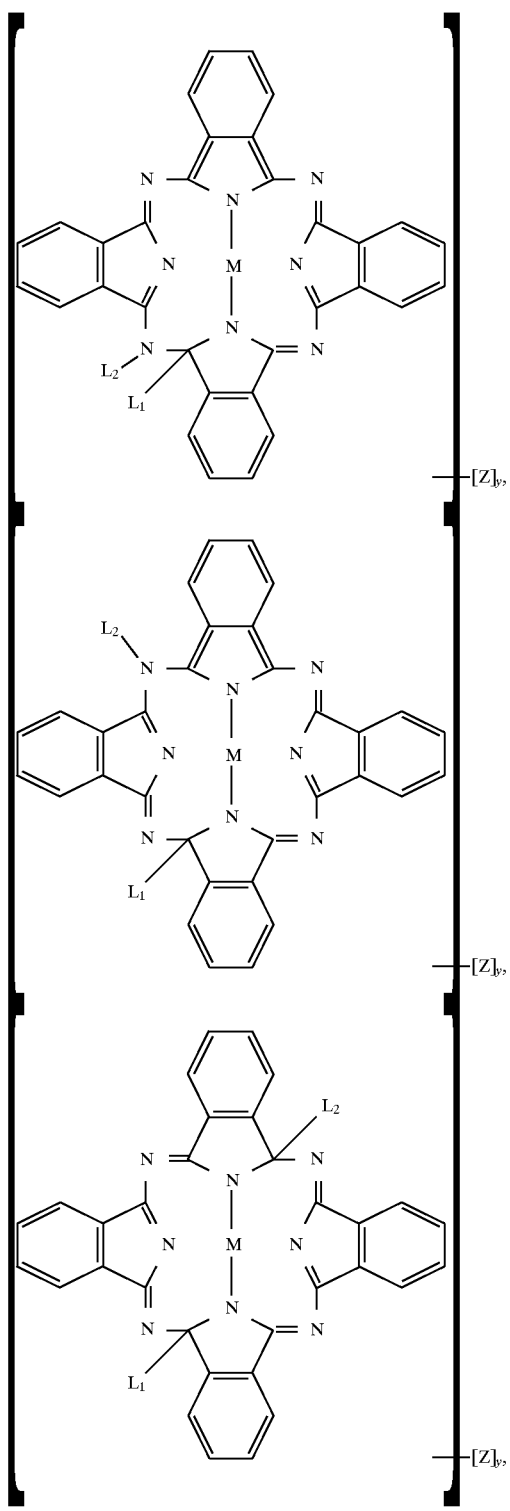
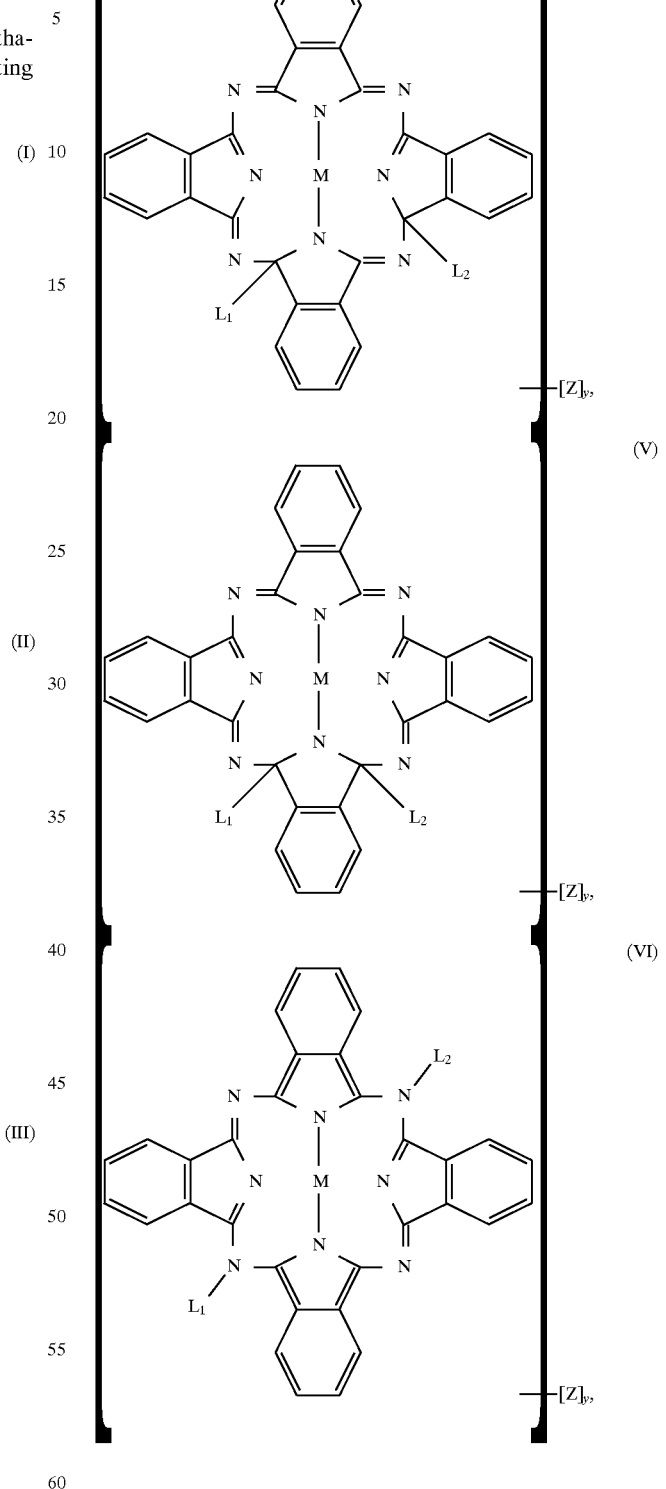

-continued

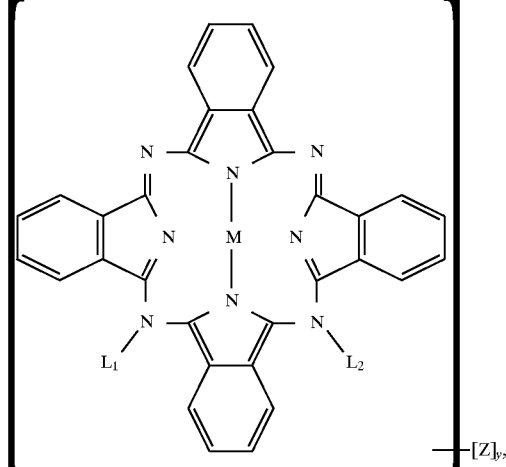

(VII)

wherein $L_1$ and $L_2$ are independently from each other $C_1$–$C_{18}$alkoxy, $C_1$–$C_{18}$alkylthio $C_1$–$C_{18}$alkylamino, $C_2$–$C_{18}$dialkylamino, or an unsubstituted or with 1 or 2 $C_1$–$C_{12}$alkyl groups substituted 5- or 6-membered imino ring which contains zero or one additional nitrogen or oxygen atom, M is two hydrogens, two metals with one valence or a metal with two or more valences, y is a number from 0 to 16, and each Z is bound to a peripheral position of the phenyl rings and is, independently of the other halogen, $C_1$–$C_{18}$alkyl, $C_1$–$C_{18}$alkoxy, $C_1$–$C_{18}$alkylthio or $C_2$–$C_{18}$dialkylamino, and using a composition comprising said soluble phthalocyanine precursor and a positive or negative resist resin, polymer or prepolymer which can be structured by crosslinking, polymerisation or depolymerization by applying heat or by irradiation (b'), and (2) locally regenerating the pigment from the above soluble precursor by thermal or photolytic treatment.

17. A method of claim 16, wherein step (2) is effectuated by laser marking.

18. A composition for making structured colour images comprising (a') a soluble phthalocyanine precursor, selected from the group consisting of compounds of formulae (I) to (VII),

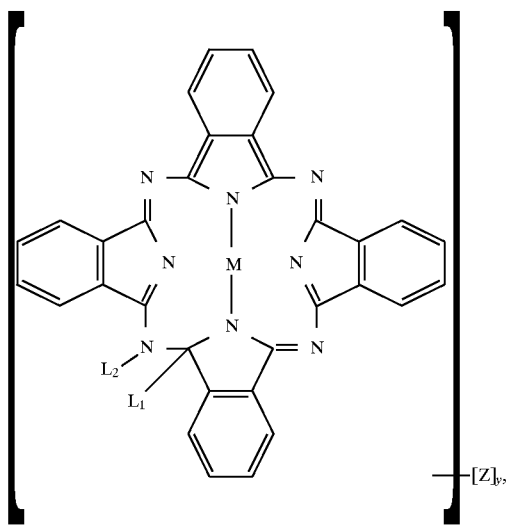

(I)

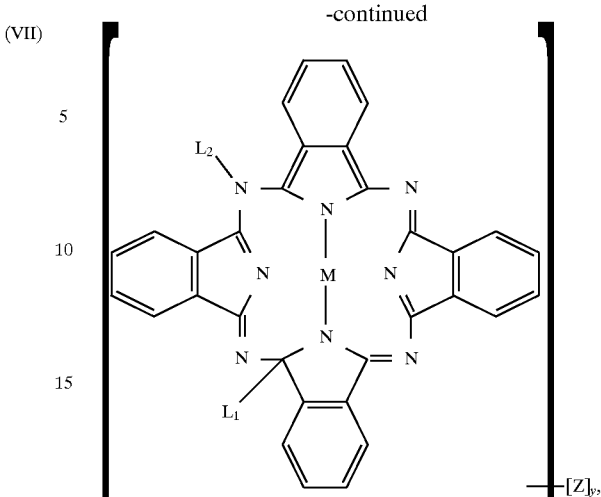

(II)

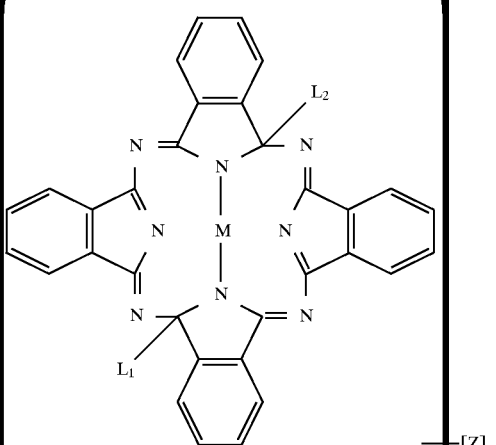

(III)

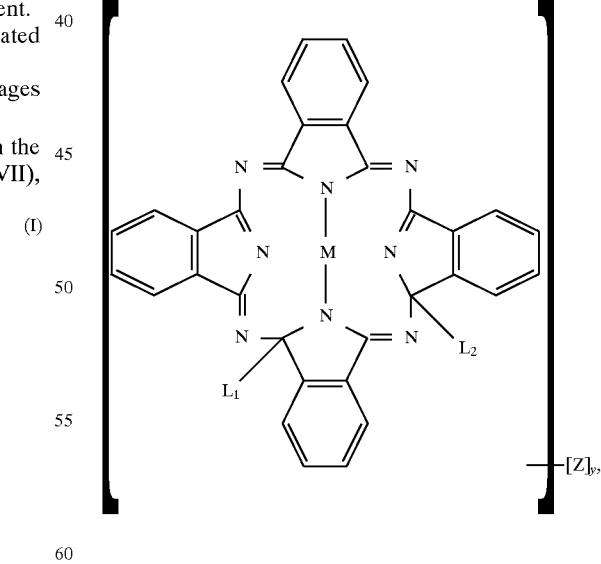

(IV)

-continued

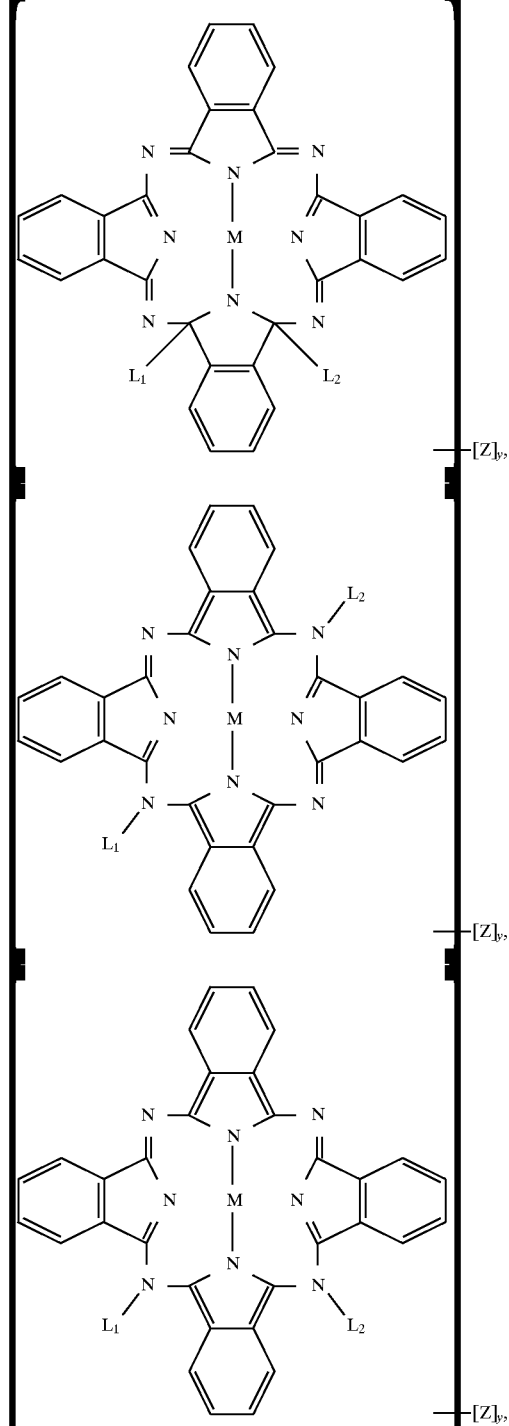

wherein L₁ and L₂ are independently from each other $C_1-C_{18}$alkoxy, $C_1-C_{18}$alkylthio $C_1-C_{18}$alkylamino, $C_2-C_{18}$dialkylamino, or an unsubstituted or with 1 or 2 $C_1-C_{12}$alkyl groups substituted 5- or 6-membered imino ring which contains zero or one additional nitrogen or oxygen atom, M is two hydrogens, two metals with one valence or a metal with two or more valences, y is a number from 0 to 16, and each Z is bound to a peripheral position of the phenyl rings and is, independently of the other halogen, $C_1-C_{18}$alkyl, $C_1-C_{18}$alkoxy, $C_1-C_{18}$alkylthio or $C_2-C_{18}$dialkylamino, and (b″) a high molecular weight binder material.

19. A method for producing coloured patterns or images including the steps of (1) forming a polymer layer containing a soluble phthatocyanine precursor, selected from the group consisting of compounds of formulae (I) to (VII),

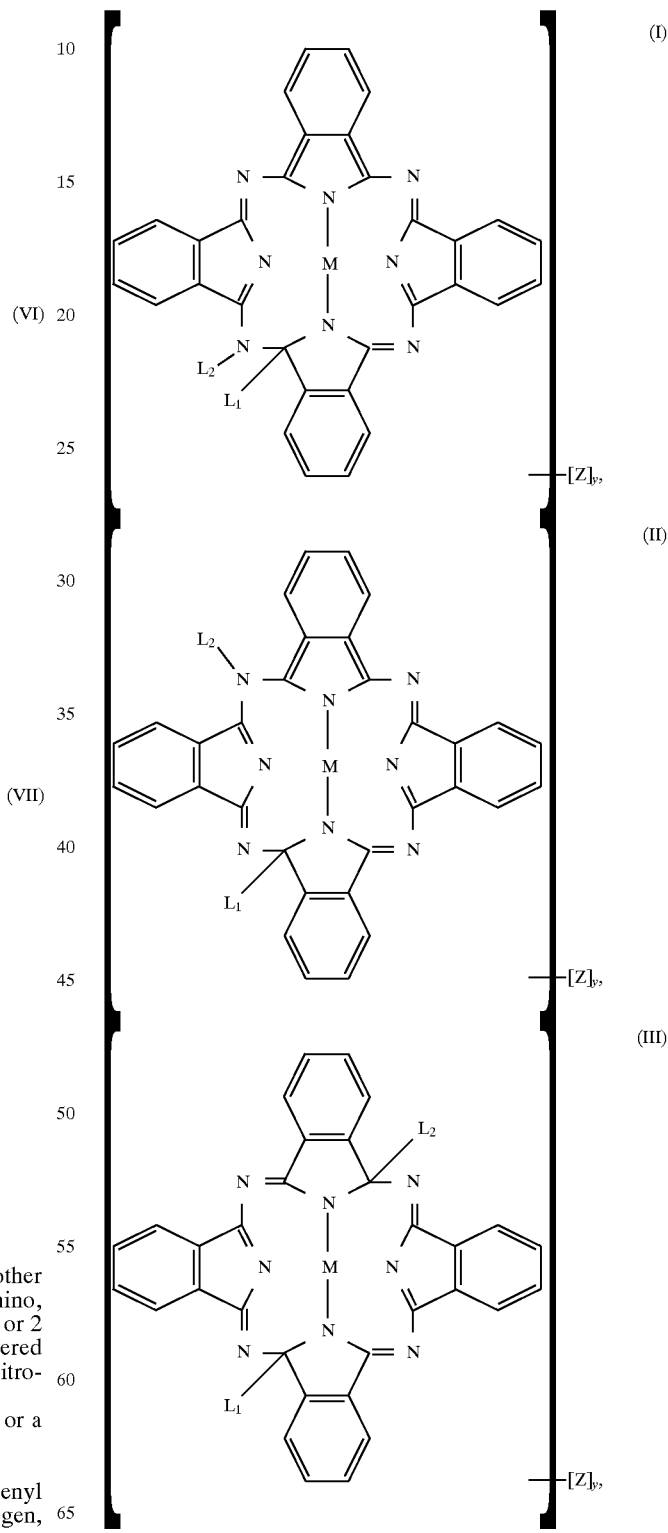

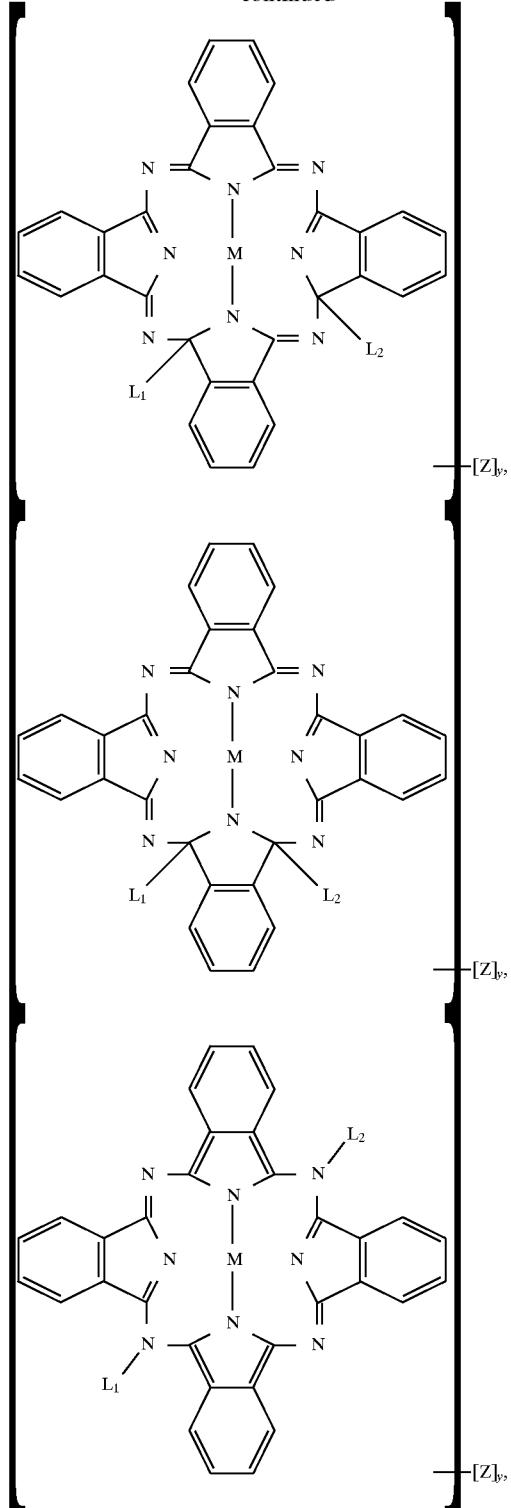

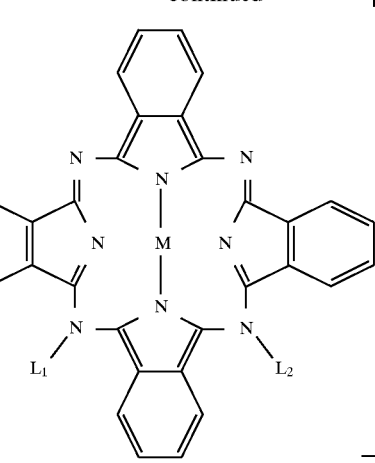

wherein $L_1$ and $L_2$ are independently from each other $C_1$–$C_{18}$alkoxy, $C_1$–$C_{18}$alkylthio $C_1$–$C_{18}$alkylamino, $C_2$–$C_{18}$dialkylamino, or an unsubstituted or with 1 or 2 $C_1$–$C_{12}$alkyl groups substituted 5- or 6-membered imino ring which contains zero or one additional nitrogen or oxygen atom, M is two hydrogens, two metals with one valence or a metal with two or more valences, y is a number from 0 to 16, and each Z is bound to a peripheral position of the phenyl rings and is, independently of the other halogen, $C_1$–$C_{18}$alkyl, $C_1$–$C_{18}$alkoxy, $C_1$–$C_{18}$alkylthio or $C_2$–$C_{18}$dialkylamino, and and a high molecular weight organic binder material (b"), and (2) locally regenerating the pigment from the above soluble precursor by thermal or photolytic treatment, wherein step (1) is accomplished by:

forming a polymer layer containing the soluble pigment precursor using a composition comprising said soluble phthalocyanine precursor and a high molecular weight organic binder material (b");

(1a) forming a polymer layer containing a high molecular weight organic binder material (b"), then (1b) ink-jetting an ink comprising a pigment precursor (a') onto the polymer layer in selected target areas; or (1a) forming a polymer layer containing a high molecular weight organic binder material (b"), then (1b) superposing a donor layer comprising a pigment precursor (a') and a high molecular weight organic binder material (b") onto the polymer layer, (1c) locally heating the donor layer to transfer the dye in selected target areas, and (1d) removing the donor layer from the receiver layer.

20. A method of claim 16, wherein said composition additionally contains a catalyst (c') for positive or negative polymer structuring the resist-type resin (b').

21. A method of claim 19, wherein said composition additionally contains a catalyst which is an acid, a base or a latent acid or base.

* * * * *